United States Patent [19]

Cherry

[11] 4,006,737
[45] Feb. 8, 1977

[54] ELECTROCARDIOGRAPHIC COMPUTER

[75] Inventor: Isaac Raymond Cherry, Mission Viejo, Calif.

[73] Assignee: Del Mar Engineering Laboratories, Los Angeles, Calif.

[22] Filed: Jan. 4, 1974

[21] Appl. No.: 430,704

[52] U.S. Cl. .................... 128/2.06 G; 128/2.06 A; 179/100.1 S; 346/33 ME; 360/5; 360/65; 360/73; 360/74; 360/90
[51] Int. Cl.² .......................................... A61B 5/04
[58] Field of Search ............... 128/2.06 A, 2.06 B, 128/2.06 F, 2.06 G, 2.06 R, 2.05 Q, 2.1 A; 346/33 ME; 179/100.1 S; 360/74, 90, 134, 65, 27, 25, 7, 5, 73; 178/66 P

[56] References Cited

UNITED STATES PATENTS

| | | | |
|---|---|---|---|
| 2,098,695 | 11/1937 | Southwick | 128/2.06 B |
| 3,228,017 | 1/1966 | Owen | 360/73 |
| 3,267,933 | 8/1966 | Mills et al. | 128/2.06 A |
| 3,395,385 | 7/1968 | Scoville | 360/5 |
| 3,552,386 | 1/1971 | Horth | 128/2.06 A |
| 3,572,316 | 3/1971 | Vogelman et al. | 128/2.1 A |
| 3,583,392 | 6/1971 | Frieberger | 128/2.09 R |
| 3,593,705 | 7/1971 | Thomas et al. | 128/2.06 A |
| 3,603,769 | 9/1971 | Malcolm | 128/2.06 G |
| 3,611,409 | 10/1971 | Glidden | 360/5 |

Primary Examiner—William E. Kamm
Attorney, Agent, or Firm—Geo. F. Smyth

[57] ABSTRACT

A multispeed ECG magnetic tape scanning device for processing and observing in a relatively short interval of time large quantities of ECG signals from two pairs of ECG leads. The information from the two pairs of leads is provided simultaneously on a single oscilloscope tube as one trace above the other, either in real time or at a high speed multiple as a superimposed ECG presentation, or superimposed on each other so as to provide superimposition of the already superimposed ECG signals. An arrhythmia bar graph is also represented on the CRT tube. The playback is in real time, or at multiple high speed playback speeds of 30, 60 and 120 times real time. The playback amplifiers have specific amplitude and frequency responses which are logically switched upon the selection of a particular playback speed to provide accuracy in the reproduced ECG information. A variable tapedeck delay loop is used in combination with two spaced playback heads to provide for a variable reaction time in switching from a high speed imposed presentation of ECG complexes to a real time reproduction to provide for writeout on a paper writer of the previously viewed superimposed ECG complexes. A digital clock using an optical encoder provides a visual presentation of time of day of recording. A programmed tape tension mechanism insures the driving of the optical encoder without slippage during rapid accelerations and decelerations of the magnetic tape. The start time of the digital display of the clock is preset to match the start time of day for the previously recorded information on the tape. The digital clock provides time synchronization of processed data for use by external devices. A heartbeat totalizer provides digital display of the number of heartbeats recorded on the magnetic tape on either an hour-by-hour basis or a cumulative basis. An arrhythmia computer detects and digitally displays the number of premature ventricular contractions (PVC) and supraventricular ectopic beats (SVT), and actuates event markers on a paper writer when the arrhythmia occurrences exceed a preselected number of occurrences during a predetermined time interval. A multispeed, multichannel, paper writer reproduces analog trend data, digital printed data and event marking. The trend information is heart rate and ST segment level to provide a scanning of an entire 24 hour tape in 12 minutes. The paper writer also displays digitally printed time of day and arrhythmia information.

64 Claims, 25 Drawing Figures

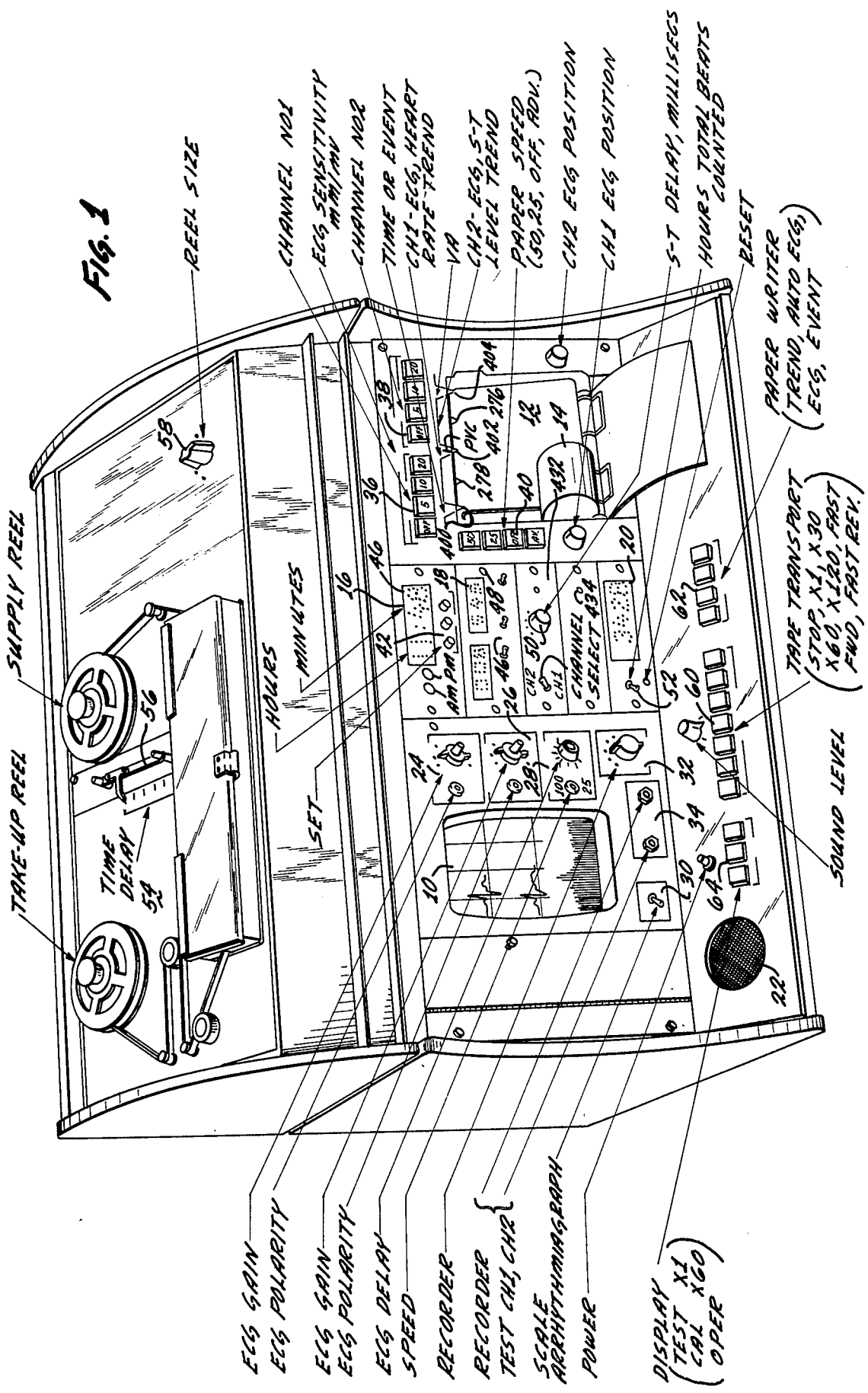

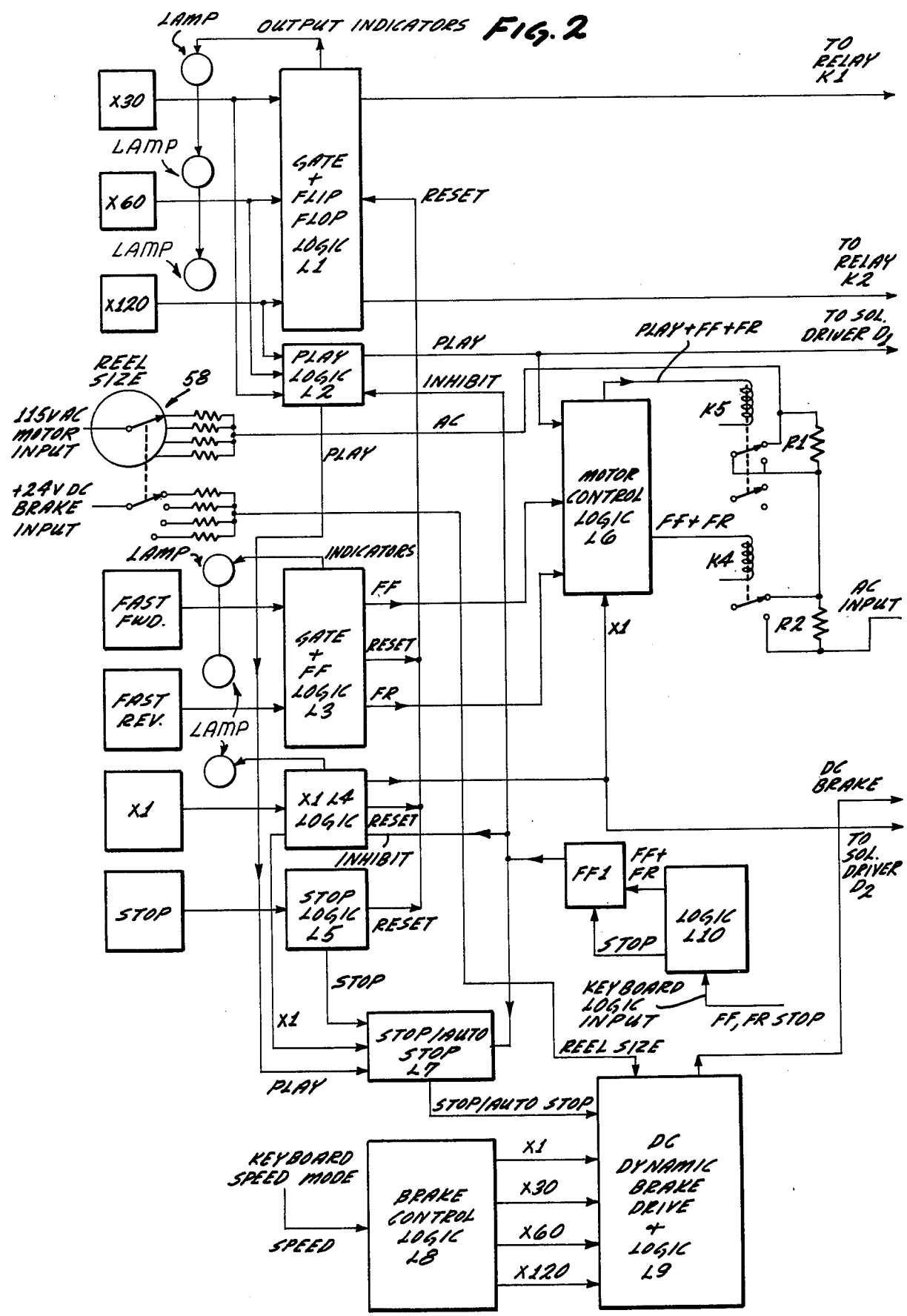

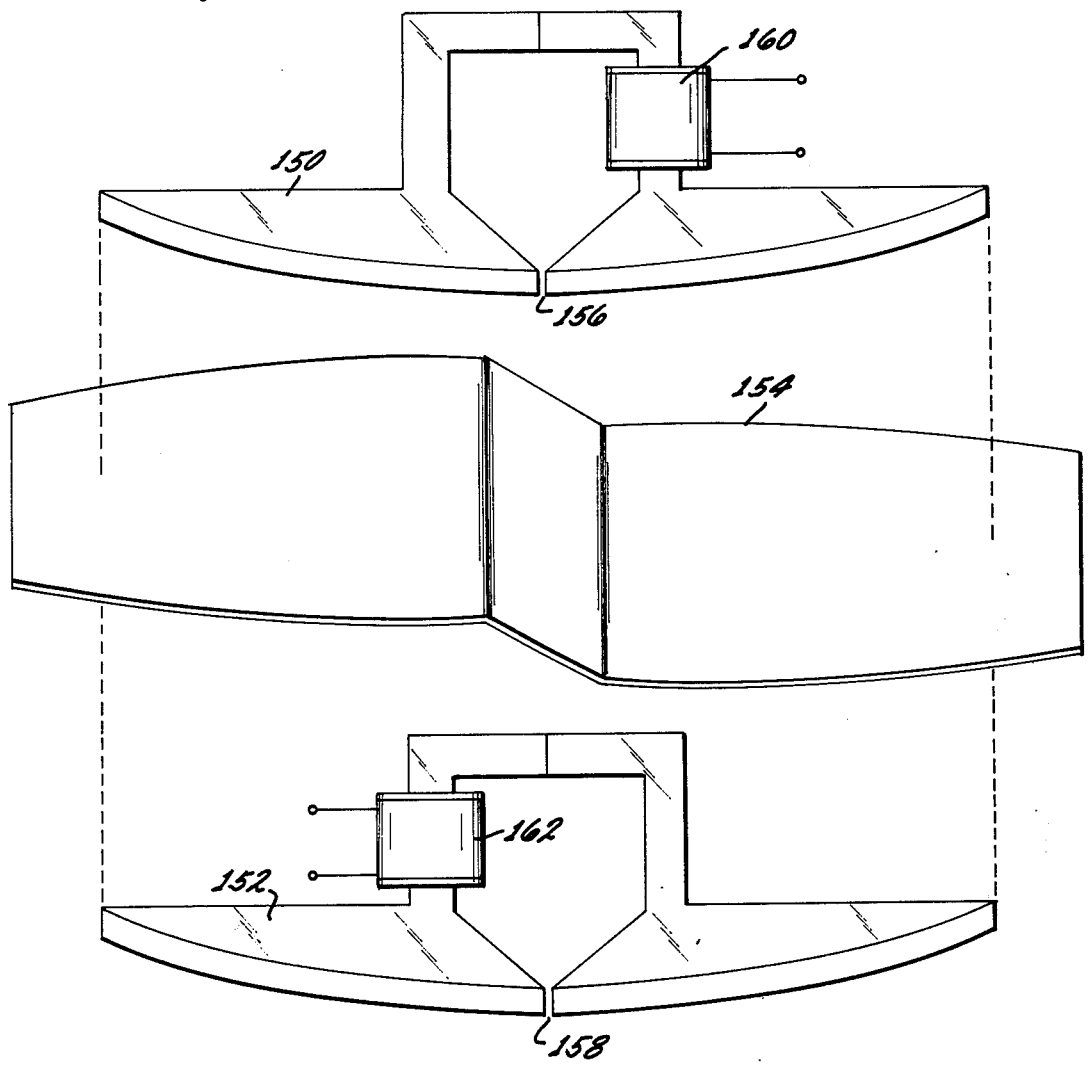
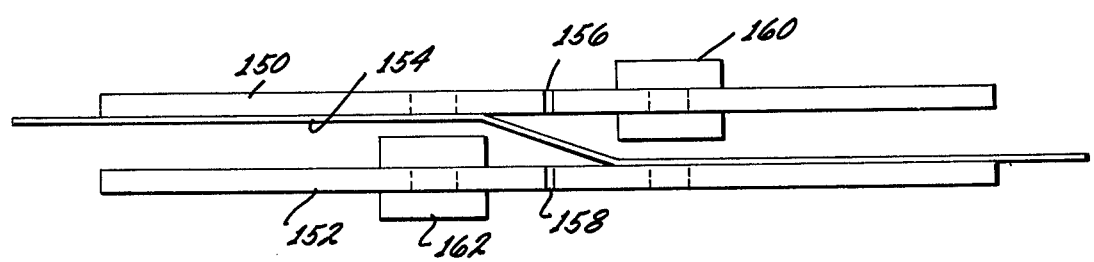

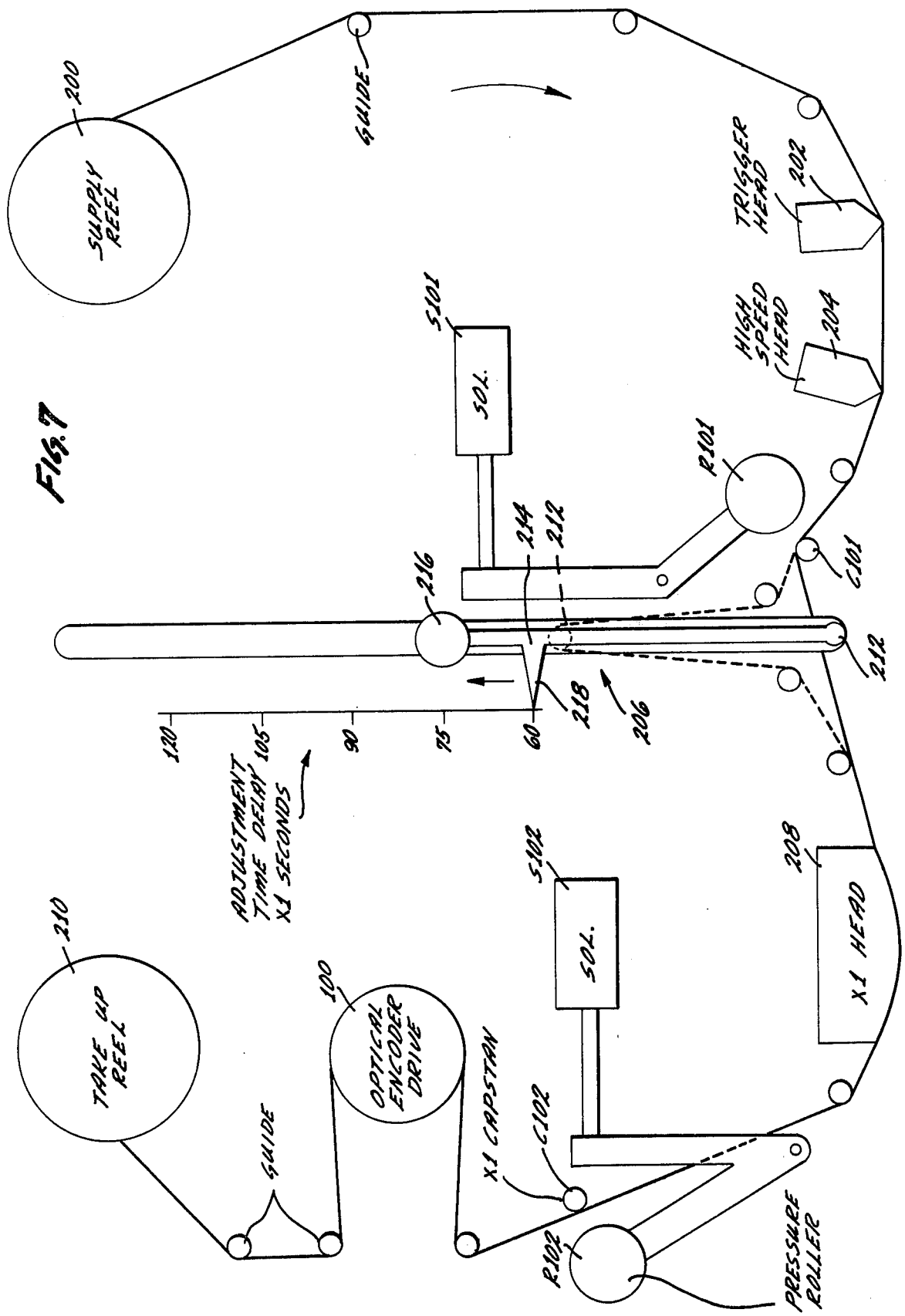

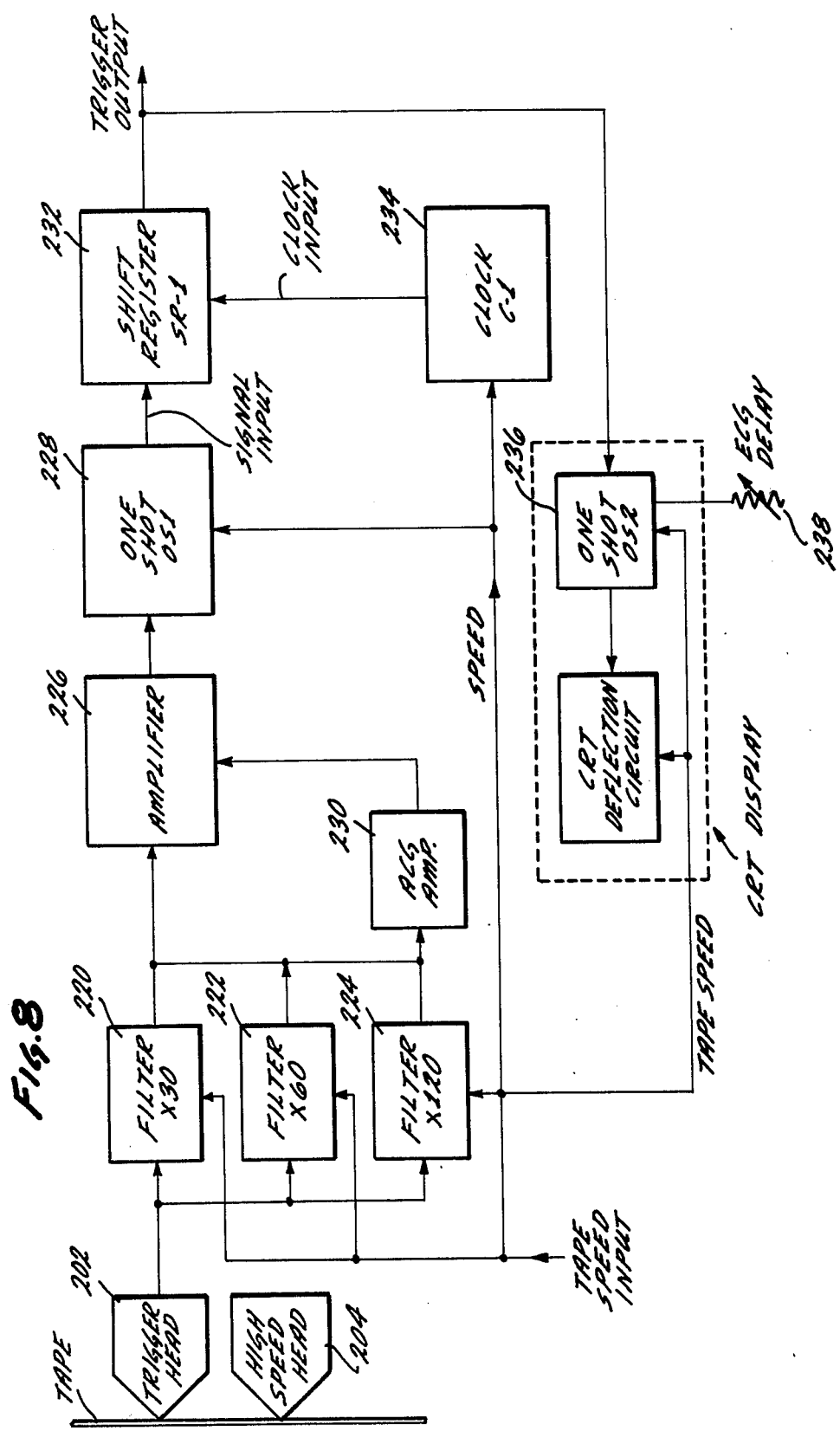

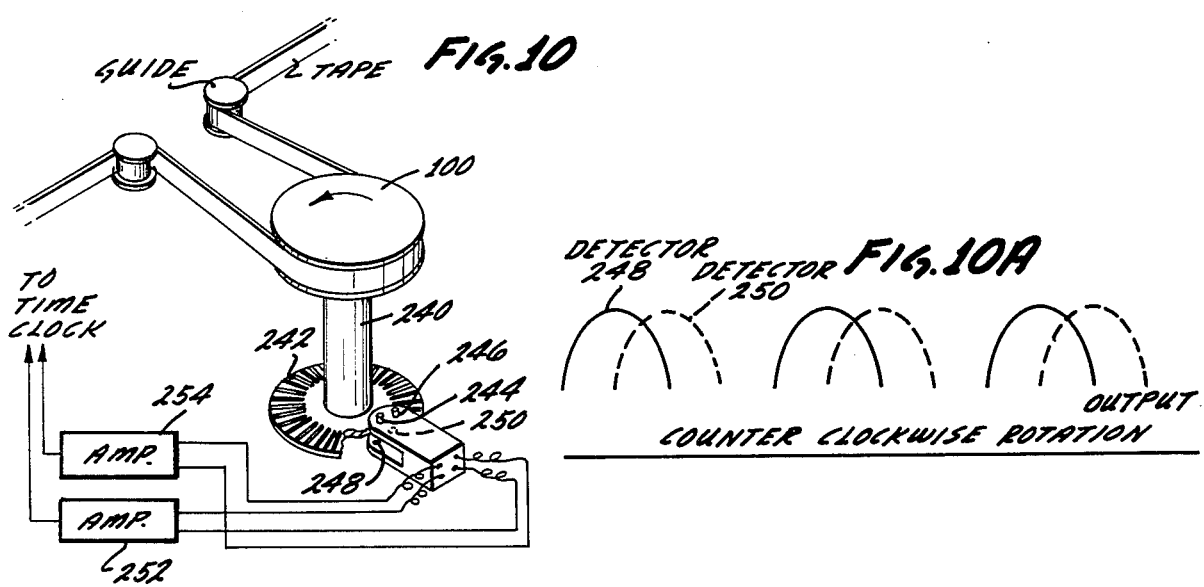
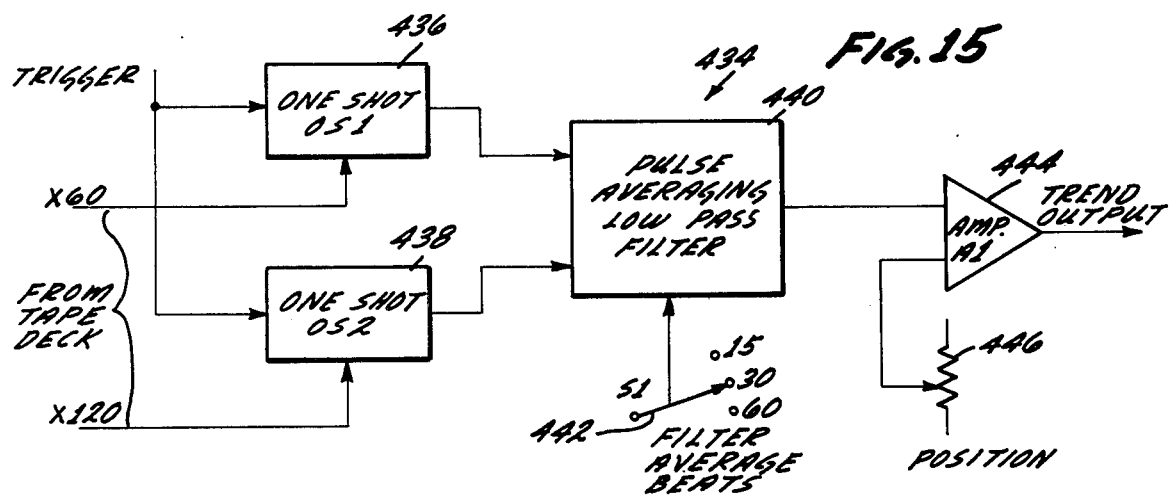
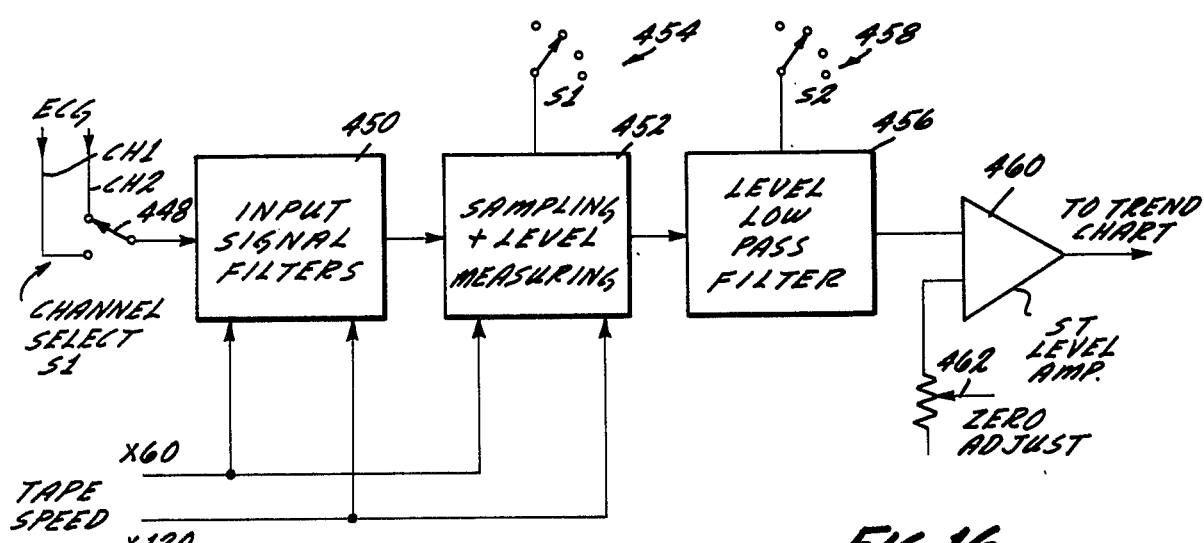

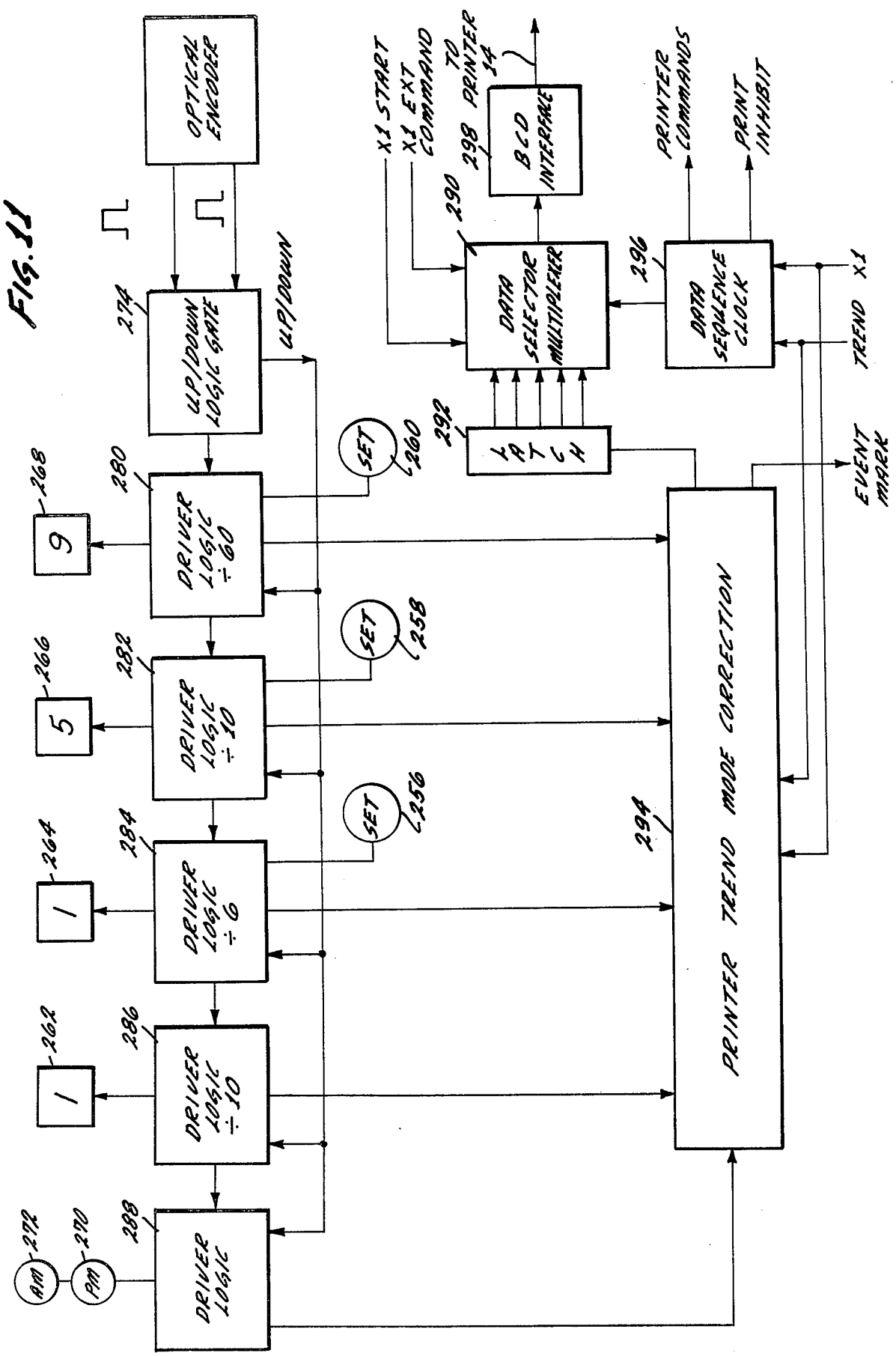

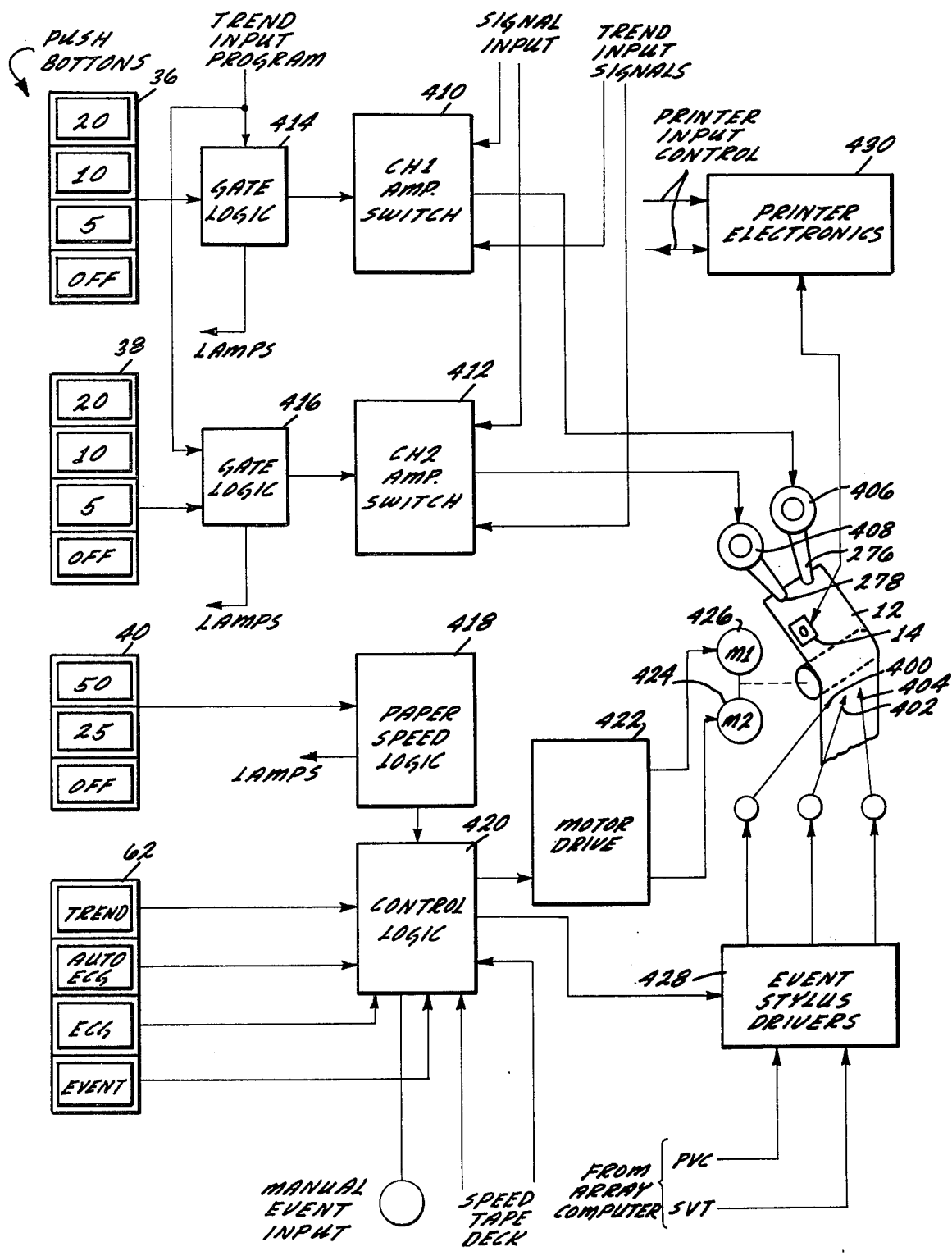

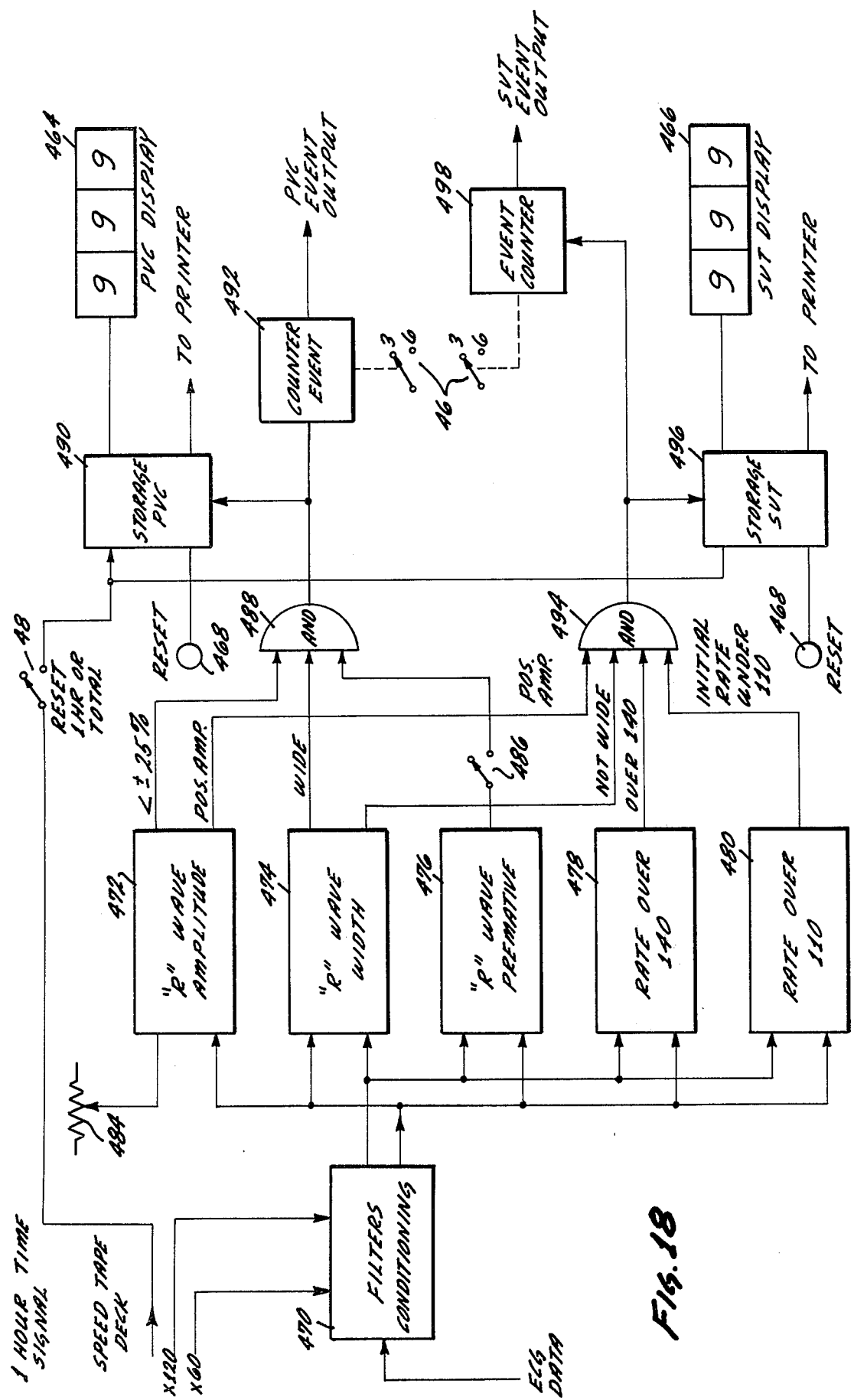

ELECTROCARDIOGRAPHIC COMPUTER

The present invention relates to an electrocardiographic computer with visual display and in particular, to a computer for processing large volumes of electrocardiac signals and for displaying and permanently recording an analysis of these large volumes of signals in a relatively short period of time.

Electrical signals that circulate upon the surface of a person's skin as a result of the expansions and contractions of the cardiac muscle are known as ECG signals. These ECG electrical signals exhibit particular waveforms and the action of the cardiac muscle and the condition of the muscle produce waveforms with particular characteristic relationships. A well-known technique in the medical field is to place electrodes on the patient's skin so as to sense the ECG signals for visual presentation. Many types of devices are currently available to provide the visual presentation of the ECG signal for viewing either in real time or for viewing at some subsequent time by a cardiologist or other trained personnel.

For example, it is possible to use a cathode-ray oscilloscope to provide for the presentation of the ECG signal either directly from the patient in real time, or at a later time from a recording of the ECG signals using a recording device such as a magnetic tape recorder. In addition, the ECG signals may be recorded by a paper writer on paper tape which is called an electrocardiograph. The graph may be subsequently viewed by trained personnel for a determination of the characteristics of the waveforms. All of these above methods provide for a fairly limited analysis of the ECG signals since the signals are generally monitored for a relatively short period of time and do not provide for the monitoring of the characteristics of the ECG signals over a long period of time, which period of time should include the normal activities of the patient.

A more desirable method of analyzing ECG signals is to accumulate large volumes of such signals and with the accumulation of the signals occurring while the patient is engaged in his normal activities. Since it would be impossible to analyze such recorded signals on a one-to-one time relationship because of the long recording period, the subsequent presentation of the ECG signals must be at an accelerated rate. This type of analysis is accomplished by recording the ECG signals in real time on a small compact tape recorder which is worn by the patient who is instructed to engage in his normal activities. The recorded ECG signals are then processed by replaying the signals at a much faster speed and with a presentation of the ECG signals on a cathode-ray oscilloscope, and with each ECG complex superimposed on the predecessor complexes. This type of superimposed replay in fast time is known as an AVSEP display and has been registered under the trademarks AVSEP and Electrocardioscanner. As a particular example of a system which may be used for the recording and playback of ECG signals with the recording in real time and with the playback in fast time, reference is made to U.S. Pat. No. 3,215,136, issued Nov. 2, 1965, in the name of Norman J. Holter, et al.

In the prior art ECG scanning device disclosed in U.S. Pat. Ser. No. 3,215,136, the superimposition of the ECG signals is accomplished by recording the same ECG signal on two different tracks of a magnetic recording tape, but with the same signals on the different tracks longitudinally displaced. The playback of the ECG signals is accomplished by using spaced magnetic playback heads for reproducing the ECG signals on the two tracks. A first one of these playback heads reproduces the ECG signals on a first one of the tape tracks for the purpose of producing a trigger signal while the second one of the playback heads reproduces the ECG signal on a visual indicator such as an oscilloscope.

The two playback heads reproduce the information which is longitudinally displaced on the two tracks so that the trigger signal which is generated from the first track synchronizes the horizontal sweep of the oscilloscope so that each ECG trace on the oscilloscope is initiated at the same point in the ECG complex. In this way each ECG trace is displayed in its entirety.

The prior art devices for providing the superimposed display as described above are capable of processing and providing a presentation of data from only one pair of ECG leads attached to the patient and these prior art devices are capable of high speed playback at only one speed. The prior art electrocardioscanning systems such as shown in U.S. Pat. No. 3,215,136 have proven to be of invaluable assistance to the cardiologist for the determination of the presence and characteristics of certain abnormalities even in view of the limited nature of the device as described above.

As an extension of the prior art ECG scanning device described above, an improvement as shown in U.S. Pat. No. 3,718,772, issued Feb. 27, 1973, in the name of Clifford Sancturay, provides for the reproduction of ECG signals from a single track magnetic tape recorder. Specifically, that reproducing system provides for recording at a very slow speed on a single track and then playing back at a high speed with provisions for the superimposition of the ECG complexes on a visual indicator such as an oscilloscope. Trigger signals to control the horizontal sweep are developed by the reproduction from the single track using a first playback trigger head. The trigger signals are delayed a particular period to provide for delayed trigger signals which control the sweep of the oscilloscope. This produces a stable superimposition of the ECG signals since the ECG signals are reproduced by a second playback head spaced from the first playback head. In this system, data is obtained from only one pair of ECG leads attached to the patient.

The present invention overcomes many of the shortcomings of the prior art devices described above to provide for an improved ECG scanning device for processing and observing large quantities of ECG signals in a relatively short interval of time, and in particular for providing an analysis of these large quantities of ECG signals. For example, the prior art ECG scanners were capable of processing and providing a presentation of ECG signals from a single pair of leads attached to the patient, whereas the present invention provides for the processing and simultaneous presentation of ECG data from at least two pairs of leads located in different positions on the patient. Since more than one pair of ECG leads attached to the patient provides the cardiologist with different views of the same cardiac activity, the simultaneous presentation of the ECG information from at least two pairs of leads provides the cardiologist sufficient information to recognize an abnormality not obvious when viewing information obtained from a single pair of leads.

As a further improvement of the present invention, the information from at least two pairs of leads is provided not only simultaneously, but is displayed on a single oscilloscope tube as one trace the other. In addition, the information from the two pairs of leads may be superimposed on each other so as to provide superimposition of the already superimposed signals obtained from the high speed scanning.

In order to increase the flexibility in the analysis of data with the ECG scanning device of the present invention, the scanner is capable of playback not only in real time, but also at multiple high speed playback speeds. For example, the present invention provides for playback speeds of 30, 60 and 120 times real time. The highest of these playback speeds is twice that previously obtained with the prior art devices so as to provide for an obvious savings of time during the analysis of the superimposed information. The lowest of these high speeds is one-half the speed of the prior art scanning devices to provide a slower presentation of the superimposed ECG complexes to allow better visual analysis of the recorded ECG information at critical times. Also, this slower playback speed allows for the ECG signal to be connected to an external digital computer and with the information occurring at a slow enough rate so that the computer can digitize the information with high resolution. The result of the multiple high speed playbacks of the present invention is to allow much greater flexibility in the use of the ECG scanner of the present invention.

In order to achieve multiple high speed playback speeds and still provide realistic waveforms from the processed ECG information, the present invention includes improvements in the tapedeck and the circuitry associated with the tapedeck to provide for proper performance. For example, the playback amplifiers have specific amplitude and frequency responses which are logically switched upon the selection of a particular playback speed so as to provide for accuracy in the reproduced ECG information. A variable tapedeck delay loop is used in combination with two spaced playback heads so as to provide a variable reaction time for manually switching from viewing superimposed ECG complexes at a selected high speed to a real time reproduction on a paper writer of the previously viewed ECG complexes. This is accomplished without the necessity of backing up the tape on the tape playback deck.

The present invention also provides an accurate time of day digital clock so that the passage of tape in both forward and reverse directions is used to control a visual presentation of time of day of recording by the digital clock. This is provided for in the present invention by the use of an optical encoder which is driven by the movement of the magnetic tape. A programmed tape tension mechanism is included to insure the driving of the optical encoder without slippage during rapid accelerations and decelerations of the magnetic tape, even with changes in speeds as well as changes in tape direction. When the speed of movement of the tape is changed, the present invention provides for the conversion of tape passage to time of day, no matter what speed. For example, the tape passage can be 1,000 times greater for a movement of the tape in fast forward or fast reverse as opposed to the movement of the tape in real time. The start time of the digital display of the time of day clock may be preset to match the start time of day for the recording of information on the tape.

The digital clock is not only used to provide a visual indication of the time of day, but is also used to provide digital outputs of the time of day to the paper writer or any other external device. The digital clock may also be used to provide time synchronization of the processed data for use by external devices such as computers, paper writers, etc.

The present invention also provides a unique form of display by combining on a single cathode-ray tube, the presentation of two superimposed high speed ECG complexes from two pairs of leads and one arrhythmia bar graph. The bar graph shows continuously the "R" wave to "R" wave interval between ECG complexes. The superimposed high speed ECG complexes may be further superimposed on each other to provide additional information to the cardiologist. The visual display uses variable time bases which are automatically controlled when switching between the playback speeds of 30, 60 and 120 times recorded time to provide the same shape ECG complexes. The apparent time base speeds may be varied between 25, 50 or 100 millimeters per second. The visual display may also be used to display the ECG signal at real time playback speed to provide a multichannel display of the ECG complexes at 25, 50 or 100 millimeters per second. In addition, the visual display includes provisions for automatically calibrating the arhythmia bar height at the various tape playback speeds to provide a direct heart rate reading independent of the tape playback speed.

The present invention also includes a heartbeat totalizer for providing a digital display of the number of heartbeats recorded on the magnetic tape. This heartbeat totalizer may provide either a display of the total number of heartbeats recorded on a complete tape, or may provide a display of the hour-by-hour total of the heartbeats. This digital display of either the total number of heartbeats or an hour-by-hour number of heartbeats is provided with the magnetic tape played back in either real time or at 30, 60 and 120 times real time when the tape is moved in Fast Forward or Fast Reverse. In order to insure that the heartbeat totalizer is accurate, the present invention provides means to subtract heartbeats from the total when the tapedeck is in Fast Reverse. This allows the identification and location of specific ECG complexes by number. The heartbeat totalizer also produces output signals of total beats or hour-by-hour beat totals for an external display such as a paper writer.

The present invention also provides an arrhythmia computer to detect and digitally display the numbers of premature ventricular contractions (PVC) and supraventricular ectopic beats (SVT). The arrhythmia computer detects the PVCs and SVTs from the magnetic tape at playback speeds of 30, 60 and 120 times the recorded speed. The arrhythmia computer provides either a display of the complete total or a display of the hour-by-hour total of the arrhythmia occurrences described above. In addition, the arrhythmia computer is designed to actuate event markers on a paper writer when the arrhythmia occurrences exceed preselected numbers of occurrences during a predetermined time interval. In addition, the arrhythmia computer may provide for a digital printout of the hour-by-hour totals of the arrhythmia occurrences.

The various printouts on the paper writer described above, plus novel trend data, which is analyzed from the recorded magnetic tape, is used with a multispeed, multichannel, paper writer for reproducing analog data, digital printed data and event marking. This multichannel paper writer has the capability of writing two tracks of ECG data from the magnetic tape which has been recorded in real time and with the writing occurring at either of two writing speeds. The two tracks of ECG data from the magnetic tape are used at high speed playback to provide two channels of trend data. These two channels of information may be the heart rate and the ST segment level so as to provide for a scanning of an entire 24 hour tape in a period as short as 12 minutes. The paper writeout of the two channels of data, representing the heart rate and the ST segment level for the entire 24 hour period is provided on a relatively short piece of paper and is provided in the short time period such as 12 minutes. The paper writer also includes the displaying of digitally printed data such as the time of day, arrhythmia and heartbeat totalization from signals generated in the ECG computer. The paper writer also provides for the automatic control of the paper speeds during the trend analysis so as to provide constant paper speed versus recorded time, even with different playback speeds. In addition, the paper writer may be rapidly switched from the high speed trend analysis to low speed ECG writeout with automatic control of the various parameters and responses.

A clearer understanding of the present invention will be had with reference to the following description and drawings wherein:

FIG. 1 illustrates an isometric view of a dynamic electrocardiography computer of the present invention, showing the front panel and the tapedeck and including a plurality of digital output indicators, an oscilloscope display and a paper writer.

FIG. 2 (a) illustrates, in more detail, the brake logic circuit shown in FIG. 2.

FIG. 4 illustrates an expanded view of a real time playback head for two channels.

FIG. 5 illustrates the same playback head from a front view.

FIG. 7 illustrates the tape loop path from the supply reel to the tape reel and including a variable delay loop.

FIG. 8 illustrates a block diagram of the tapedeck trigger system for use in controlling the sweep of the superimposed oscillograph display.

FIG. 10 illustrates the optical encoder for use in providing a clock signal in accordance with tape movement, and FIG. 10 (a) are waveforms used in explaining the operation of the optical encoder of FIG. 10.

FIG. 11 is a block diagram of the digital clock and including the clock display.

FIG. 14 illustrates a block diagram of the paper writer control system.

FIG. 15 illustrates a block diagram of a heart rate trend system to produce a trend output for the paper writer.

FIG. 16 is a block diagram of an ST level system to produce a trend output for the paper writer.

FIG. 18 illustrates a block diagram of the arrhythmia analyzer for supplying signals to the front panel shown in FIG. 17 and to the paper writer.

Figure 2:
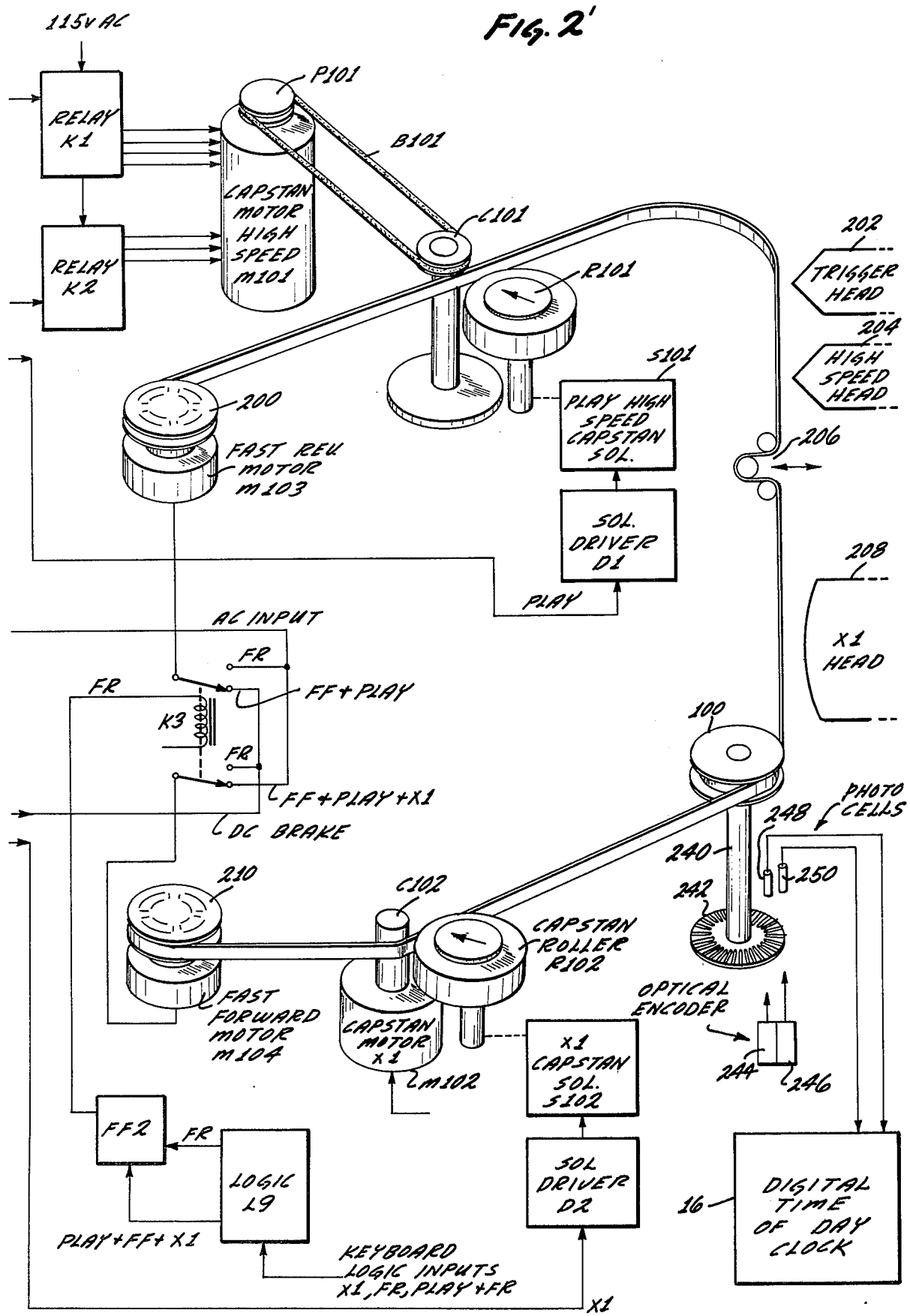
FIG. 2 illustrates a block diagram of the tapedeck control logic circuit for providing control of the tapedeck at various speeds and in various directions in accordance with keyboard actuations.
Figure 2:
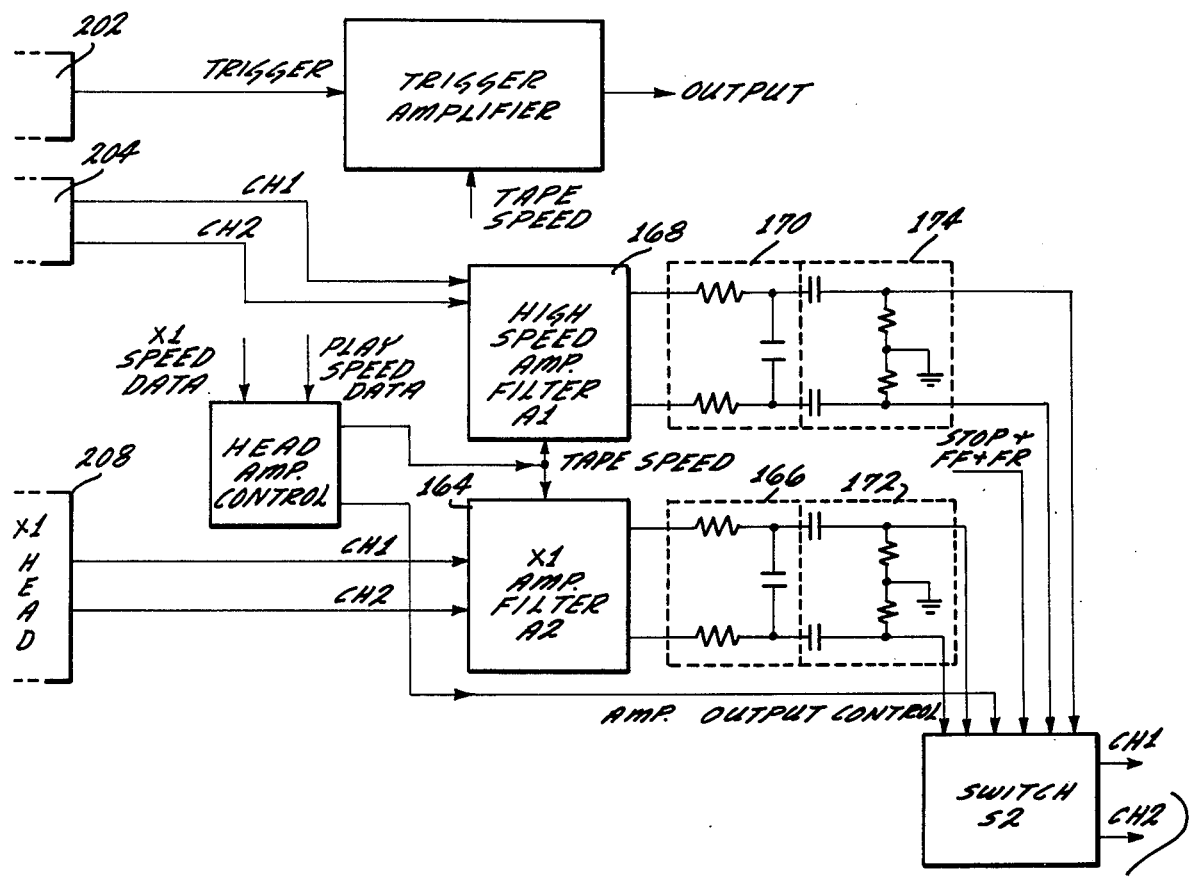

In FIG. 1, an electrocardiocomputer of the present invention is shown. This computer provides for two channel playback of superimposed high speed ECG complexes and an arrhythmia bar graph all in the same oscilloscope display section 10. A two channel paper writer 12 includes in addition to the two channels of information, a plurality of event markers and a digital writer 14, to print digital information. In addition to the oscilloscope and paper writer, various digital displays are provided on the front panel, which include a digital time clock 16, an arrhythmia analyzer 18, and a heartbeat counter 20. An audio output may be provided by a speaker 22.

The various displays are controlled by control knobs and switches located adjacent to the display. For example, control sections 24 and 26 control the gain and polarity of the two channels of ECG information. Control section 28 controls the trigger delay for the sweep of the superimposed ECG complexes and also controls the speed of the sweep to widen the trace. The scale of the arrhythmia bar display is controlled by control section 30. A control section 32 varies the input amplitude of the signal from the recorder. The input from the two channels of the recorder may be connected directly into the input jacks in section 34 in order to provide for a recorder test.

The paper writer 12 may also include controls such as controls 36 and 38 to vary the sensitivity of the paper writer in the two channels. The paper speed may be controlled by a group of push buttons 40.

The digital time clock includes setting buttons 42 to set the time and setting buttons 44 to set either AM or PM. The arrhythmia analyzer includes switches 46 to control a predetermined number of events per minute to be exceeded, and a switch 48 to control the totalizing either in an hour period or cumulatively. The ST level trend computer includes an ST delay control 50. The heartbeat computer includes a switch 52 for either one hour totals or cumulative totals.

The tape transport section 54 includes a variable delay tape loop 56 and an adjustment switch for different reel sizes 58. In addition, the master panel includes a plurality of push buttons 60 to control the tape speed and direction. A plurality of push buttons 62 control the paper writer to provide different output writing modes. A series of push buttons 64 provide a control of the oscilloscope display.

It is to be appreciated that the above description of the overall outward appearance of the ECG computer of the present invention is general in nature and in many instances, more specific details will be included at a later portion of this specification. For example, not every control element has been described and some elements which have been described are self-evident and conventional in their operation and may not be described in much greater detail.

Generally, the ECG computer of the present invention is a high speed ECG scanning device that documents abnormalities from a long term ECG recording such as a recording over a 24 hour period using two pairs of leads to provide two channels of ECG information. This ECG information may be displayed in superimposed form at 30, 60 or 120 times real time, or as normal ECG traces in real time on the display oscilloscope 10. This display oscilloscope 10 provides a single multiscan display to provide both ECG traces and an arrhythmia bar trace simultaneously on the same cathode-ray tube.

The digital time clock 16 accurately displays tape time and relates it to the time of recording when preset at the start of the tape. A two channel paper writer 12 provides documentation of the ECG data being reviewed in the ECG real time mode. The time of day of each selected paper writeout is automatically printed on the electrocardiograph paper.

In addition to the writeout of the ECG data, the ECG computer includes specific analysis sections 434 and 432 to obtain heart rate and ST segment data from either of the ECG lead positions. This data is fed to the paper writer 12 when the tape is programmed to be in the high speed mode to provide a trend chart of heart rate and ST segment in as little as 12 minutes from a 24 hour recording.

The heartbeat counter 20 provides the total number of heartbeats which occur either on an hour-by-hour basis or on a cumulative basis. The arrhythmia analyzer 18 provides digital displays of the numbers of ventricular and supraventricular ectopic beats that occure on either a per-hour basis, or on a cumulative basis. This data may also be recorded digitally on the paper writer by the digital writer 14.

As shown in FIG. 1, a group of push button switches are shown at position 60 to control the operation of the tapedeck. FIG. 2 illustrates these same push buttons for use in controlling the tapedeck control logic system. The push button switches are momentary contact typewriter-type keys, which include built in indicators so as to provide a memory visual display of the present keyboard state. The push buttons are labeled, "Stop", "X1", "X30", "X60", "X120", "Fast Forward", and "Fast Reverse". The Stop key does not have an indicator lamp. The general operation of the control of the tapedeck in accordance with the particular key activated and with reference to FIG. 2, is as follows:

In the Stop mode, the tape does not move, but one of either motor M103 and M104 has torque to pull the tape. The other one of the motors M103 and M104 acts as a DC dynamic brake to hold the tape in a Stop position. The motor which acts as a DC dynamic brake is controlled to provide a force slightly larger than the takeup torque value. Either of the motors M103 or M104 may act as the brake, depending on the previous running state of the tape transport. For example, if the previous state was fast forward (FF) or playback at any speed, then after the stop button is operated, the torque remains on the fast forward motor M104. If the previous state was fast reverse (FR), then after the stop button is operated, the torque would remain on the fast reverse motor M103, and the brake would be provided by the fast forward motor M104. The above described system provides a tape-tensioning design to keep the tape tight around the tape loop at all times. It is especially important that the tape is tight around a clock pulley 100 which pulley is used to drive an optical encoder to produce a clock time signal.

In the X1, or real time mode, the X1 capstan roller R102 is controlled by the X1 capstan solenoid S102 to move towards the magnetic tape and engage the X1 motor capstan C102. In this mode, the fast forward motor M104 is operated at low torque and the fast reverse motor M103 acts as a dynamic brake.

In the X30, X60 and X120 high speed playback modes which are 30, 60 and 120 times real time, the high speed capstan roller R101 is activated by the high speed capstan solenoid S101 to move toward the magnetic tape and engage the high speed capstan C101. The fast forward motor M104 is operated at a higher torque than in the X1 mode. The fast reverse motor M103 acts as a dynamic brake, but at a lower value than in the X1 mode, since the supply reel of tape 200 is moving at a greatly increased speed. By activating the desired one of the X30, X60 or X120 keys, the speed of the high speed capstan motor is controlled to operate either at 900, 1,800 and 3,600 rpm.

In the Fast Forward and Fast Reverse mode, a large torque is applied to the applicable motor and with a small dynamic brake to the other one of the motors. This keeps the tape tight during starting and fast rewind, so that the tape does not slip around the digital clock pulley 100. If the direction of fast rewind is changed from fast forward to fast reverse, or from fast reverse to fast forward, the torque and dynamic brake are also reversed, so that the tape reverses direction without throwing a tape loop. The tape first stops slowly, then increases in speed since the motors are controlled to always have one reel pulling and one reel holding back independent of the direction of tape travel.

In order to change from one mode to another, the logic design of FIG. 2 is designed to provide rapid mode changing from any condition without a tape loop or loss of tension. This is important, since a loss of tension around the clock pulley 100 would cause time errors. To achieve this, the design has certain automatic features that prevent particular conditions from occurring. For example, during rapid fast forward tape travel, it is impossible to activate the X1, X30, X60 and X120 keyboard switches. Such an activation would cause a tape foul-up, since the tape would still be moving at a high speed and depending upon the reel size, and the amount of tape on the reel, the normal inertia may keep the reel moving several seconds. This would be true for either Fast Forward or Fast Reverse mode, so that the system of FIG. 2 includes memory circuits that make the tapedeck automatically go to a Stop mode if any other key such as X1, X30, X60 and X120 is activated after a Fast Forward or Fast Reverse mode.

As indicated above, the system is specifically designed to keep adequate tape tension around the digital clock pulley 100 under all possible modes of operation or changes from any mode to any other mode. This it to insure that the pulley 100 accurately moves in relation to tape movement to provide for a reliable indication of the time of day relative to the tape position once the initial starting time for the tape has been preset.

As shown in FIGS. 1 and 2, a rotary switch 58 is used to adjust the take-up torque for operation in either Fast Forward or Fast Reverse and also adjust the dynamic brake used in stopping the tape and in the playback of the tape for reel sizes of 1¾, 3, 4 and 7 inch.

Turning specifically to FIG. 2, the motor M101 is a three speed synchronous motor that runs at either 900, 1,800, or 3,600 rpms to connecting poles in the motor in different configurations. This type of motor is commercially available and one such motor which is available bears model number NCH-13, B7122XZ, 115V, 50/60 HZS, 900/1800/3600, and is manufactured by the Bodine Electric Company of Chicago, Illinois. This motor uses a total of 7 input wires and by varying the connection to these input wires, gives the three desired speeds of 900, 1,800 and 3,600 rpms. The motor M101, is connected through a pulley P101 and a drive belt B101 to drive the high speed capstan C101, to as to provide tape speeds of 3¾, 7½ and 15 inches per second. The X30, X60 and X120 push buttons change the logic circuit L1 to provide output signals to two relays K1 and K2, which in turn provide the proper connections to the motor M101 to produce the three speeds. Motor M101 is controlled to always run at one of its three speeds and may then be changed to any other speed. Since the motor is always maintained at its last operational mode speed, a fast transfer may be made to any other speed since the motor is already moving and does not have to be started from a rest position. The speed modes may therefore be rapidly changed with minimum delay to provide very rapid analysis between a high speed superimposed scan and a low speed X1 writeout.

The motor M102 is used to drive the tape at X1 speed and uses a capstan C102 which is separate from the high speed capstan C101. The X1, or real time speed of the tape is 7½ inches per minute which provides for the recorded tape containing information for a long period of time, such as 24 hours. As indicated above, the two motor M103 and M104 provide fast reverse and fast forward functions.

The fast playback motor M101 generally provides for the three different playback speeds of X30, X60 and X120, by the use of an 8 pole motor and by choosing either two, four or eight poles within the motor to provide the different speeds of rotation. The keyboard switches, X30, X60 and X120 provide momentary signals which activate the logic block L1 to set it in any one of three states. In addition, as shown in FIG. 2, reset inputs from any of the other keyboard contacts shown in FIG. 2 return the logic L1 to the initial state.

Figure 3:
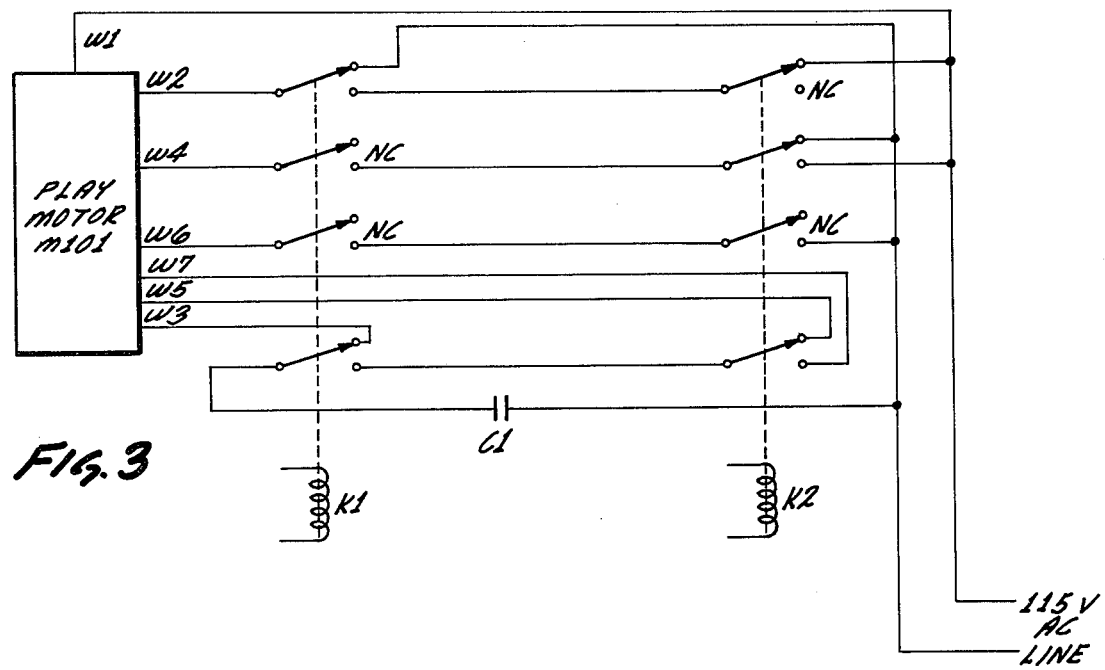
FIG. 3 illustrates a schematic of the relay and motor interconnections to provide control of the motor at various speeds.

As indicated above, the drive motor M101 is commercially available and includes 7 input wires designated W1 through W7. The specific interconnection of the AC line voltage by the relays K1 and K2 to the wires W1 through W7 is shown in FIG. 3. The relays K1 and K2 are controlled by signals from the logic block L1. The relays K1 and K2 in combination provide multipole double throw contacts to insure rapid switching from one speed to another without the use of rotary selectors. Specifically, the desired output speed for the motor M101 is obtained by the interconnection of the windings W1 through W7 using four pole double throw contacts. The logic block L1 controls the relays K1 and K2 in the following relationship and where the speed "S" at the different high speed playback speeds is as follows:

$$S\ X30 = \overline{K1} \cdot \overline{K2}$$

$$S\ X60 = K1 \cdot \overline{K2}$$

$$S\ X120 = K1 \cdot K2$$

FIG. 3 specifically shows the interconnection of the 7 wires, W1 to W7, to the multipole contacts controlled by the relays K1 and K2. At the X120 speed, one side of the AC line is connected to windings W1 and W4, the other side of the AC line is connected directly to winding W6 and the other side of the AC line is connected through the starting capacitor C1 to winding W7. The capacitor C1 is used to apply starting torque to the motor M101. With this interconnection the motor operates as a two pole motor at 3,600 rpms. At the X60 speed, one side of the line is connected directly to the windings W1 and W2 and the other side of the line is connected directly to the winding W4 and through the starting capacitor C1 to the winding W5. With this interconnection the motor operates as a four pole motor at 1,800 rpms. At the X30 speed, one side of the AC line is directly connected to winding W1 and the other side of the AC line is connected directly to the winding W2 and through the capacitor C1 to winding W3. The motor now operates as an eight pole motor at 900 rpms.

The motors M103 and M104, shown in FIG. 2, are used to transport the magnetic tape in either direction during the Fast Forward or Fast Reverse commands. The motor M104 is also used to drive the tape take-up reel during the normal Play mode. During Fast Forward or Fast Reverse, the two capstans C101 and C102 are not activated. A relay K3 is activated in the Fast Reverse mode to apply the line voltage to the motor M103. At this time, dynamic braking is applied to the motor M104 to keep the tape tight across the heads and around the clock pulley 100.

In the Fast Forward, or Play modes, at either the X1, X30, X60 or X120 speeds, AC line voltage is applied to the motor M104, using relays K4 and K5 and in accordance with the position of the reel size switch 58. As shown in FIG. 2, the reel size switch 58 varies the voltage input in predetermined increments in accordance with a group of resistors. The relays K4 and K5 are used to short out the resistors R1 and R2 so as to drop the AC voltage to different levels to provide different take-up torques. For example, a torque level "A" allows Fast Forward or Fast Reverse operation with relays K4 and K5 activated. A torque level "B" which is slightly lower is used during high speed playback at the X30, X60 and X120 speeds and is provided only when relay K5 is activated. A torque level "C" is used to provide a take-up torque for the X1 mode or the Stop mode and is provided when neither of the relays K4 or K5 is activated.

The control logic system for the tape transport is shown in FIG. 2 as a plurality of logic blocks L1 to L10. Each logic block is formed from a plurality of conventional logic gates and flip-flops. It is to be appreciated that the interconnection of these logic gates and flip-flops to form logic blocks L1 through L10 is of conventional design and will generally be described using logic equations. These equations are fully representative of the particular functions of these blocks and since the specific design of the logic blocks in and of themselves form no part of the invention, these equations and other descriptions are used to avoid excessive length in the description of the present invention.

The logic blocks L1, L2, L3, L4 and L5 are connected to the 7 push button switches shown in FIG. 2 and with each logic block including a flip-flop memory so as to hold the last state of operation. In addition, each of the 7 push buttons resets the other logic blocks so that any condition may be maintained.

As indicated above, the logic block L1 decodes the X30, X60 and X120 buttons to activate relays K1 and K2 to achieve the three motor speeds form the motor M101.

Logic blocks L3 and L6 work in combination with the keyboard inputs Fast Forward and Fast Reverse and X1 and Play (where play = X30 + X60 + X120) to control relays K4 and K5. The operation of the relays K4 aND K5 control the take-up torque "T" at three levels A, B, or C, of either the fast forward or fast reverse motors. The three levels of torque described above follow the logic equations, $$\text{Torque A} = FF + FR = K4 \cdot K5$$

$$\text{Torque B} = (\text{Play X30} + X60 + X120) = \overline{K4} \cdot K5$$

$$\text{Torque C} = \text{Stop} + X1 = \overline{K4} \cdot \overline{K5}$$

The logic block L5 is a simple set-reset flip-flop which stops the tape motion by resetting all other logic groups, releasing the capstan pressure roller, setting up the condition for the low torque level torque C on either the fast forward or fast reverse motor and increasing the DC dynamic brake on the supply motor.

The logic groups L2 and L4 determine the status of the high speed capstan C101 and the low speed capstan C102 and provide outputs to the applicable capstan drives D1 and D2. These capstan drives D1 and D2 in turn drive the high speed capstan solenoid S101 to activate the high speed capstan roller R101, or to drive the X1 capstan solenoid S102 to activate the X1 capstan roller R102. The logic equations provided by logic groups L2 and L4 in accordance with the activation of particular keyboard inputs are as follows:

$$\text{Play} = D1 + (X30 + X60 + X120) \overline{I}$$

$$X1 = D2 \cdot \overline{I}$$

where
I = Inhibit after FF and FR

An inhibit signal I from logic group L10 and flip-flop FF1 is also applied to logic groups L2 and L4 so as to prevent the capstan solenoids from being applied immediately after the tape is moving at high speed in either the Fast Forward or Fast Reverse mode. If either of the capstans were activated while the tape was traveling at high speed, tape breakage could occur. The inhibit signal I is formed from the memory flip-flop FF1. Specifically, the memory flip-flop FF1 is set to one state after either a Fast Forward or Fast Reverse operation and may only be reset by the activation of the Stop mode. Therefore the tape transport may only go to a Stop mode after a Fast Forward or Fast Reverse mode to thereby prevent damage to the tape.

The logic block L9 receives Fast Forward, Play and Fast Reverse keyboard inputs to control the flip-flop FF2 and the relay K3. The relay K3 is a reversing relay so as to control which one of the motors M103 and M104 is used to provide torque and which one is used to provide brake.

If TM103 = Motor M103 in Torque

TM104 = Motor M104 in Torque

BM103 = Motor M103 in Brake

Ti BM104 = Motor M104 in Brake, then,

TM103 = FR = K3

TM104 = FF + Play + X1 = $\overline{K3}$

BM103 = $\overline{TM103}$

BM104 = $\overline{TM104}$

The logic group L7 in combination with the fast forward and fast reverse inhibit signal I from FF1 and in combination with the play logic L2 and the X1 logic L4 is used to provide an automatic stop feature. For example, if improper operational procedures are followed, wherein any one of four keys if depressed (X1, X30, X60 or X120) after the Fast Forward or Fast Reverse mode, then an automatic Stop mode is initiated as defined below.

I = Inhibit after FF and FR

As = Auto Stop = (X1 + X30 + X60 + X120) I

Figure 2A:
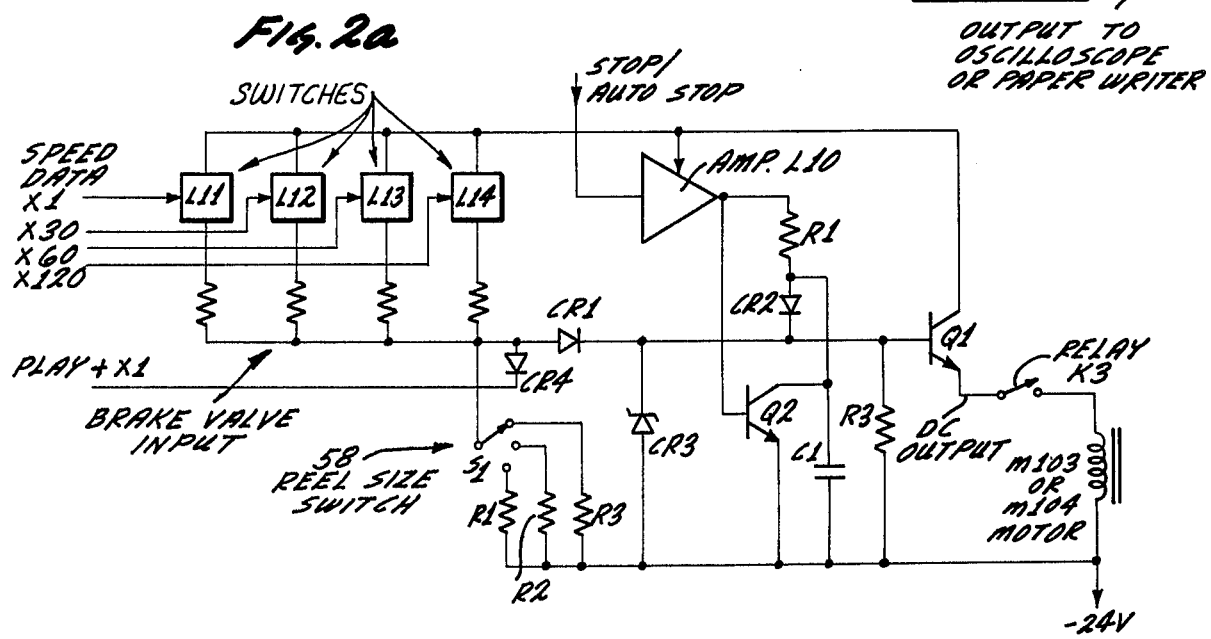

In order to stop the motion of the tape, move the tape smoothly at the various speeds, and to hold the tape tight when stopped, the system of FIG. 2 includes dynamic and static braking. This braking is accomplished using a DC current from a current source which is applied to the windings of the AC torque motors M103 and M104. The current is switched from the output of the dynamic brake logic block L9 by the relay K3 to either one of the motors M103 or M104. The brake output circuit includes an emitter follower Q1 as shown in FIG. 2A which is capable of high current output. This current when passed through an AC torque motor causes the rotor to drag due to eddy currents and magnetic hysteresis and the current is of sufficient magnitude to perform high speed braking even for the large reels of tape. A reduced amount of braking current is used during the normal play operation or when the tape transport is in a Stop mode.

The operation of the braking circuit is that one of the motors act as a brake while the other motor acts as a take-up motor to provide that tape tension is always maintained during any mode or during a change from any mode to any other keyboard mode. This insures that the digital clock pulley 100 accurately follows the movements of the tape. Sufficient tension around the clock pulley 100 is maintained during rapid starting, rapid reversing, normal play speeds of X1 through X120, changing speeds from X1 through X120, and during rapid stopping.

The logic blocks L8 and L9 obtain either speed or mode data from the various keyboard entries and logic outputs. In addition, the reel size switch 58 also is used as an input to the logic block L9 to control the amount of braking during different modes of operation. The output of the logic block L9 sets up the following braking conditions where:

BA = Brake to Stop after FF and FR
BB = Brake on X1 speed
BC = Brake on X30 speed
BD = Brake on X60 speed
BE = Brake on X120 speed
BF = Brake on FF and FR The amount of braking required during the movement of the tape at the X1, X30, X60 or X120 speed is different due to factors of friction and due to the effectiveness of the hysteresis braking of the motors M103 and M104 and therefore the amount of braking must be varied for each speed. The different braking factors is accomplished by applying different voltages to the emitter follower Q1 shown in FIG. 2A which in turn controls the flow of current to the appropriate motor. The different braking modes provided by the system of FIG. 2 and 2A are as follows:

In the BA braking mode, maximum DC current flows through the supply motor which is either M103 or M104, depending on tape direction. This maximum DC current causes rapid tape stoppage without losing tension of the tape. The final value of braking exceeds the take-up torque of the take-up motor and therefore the tape stops and remains under tension.

In the BB through BE braking modes different brake values are supplied to the motor M103 to keep the proper amount of tension on the tape. This tension must be sufficient to maintain the drive of the clock pulley 100 and to keep the tape in close contact with the heads such as the trigger head, the high speed head, or the X1 head as shown in FIG. 2.

In the BF mode a small amount of brake current is allowed to flow through the appropriate motor to maintain the tape tight around all pulleys and especially the clock pulley 100.

The various brake current conditions may be defined as follows:

BA = EA . Z where Z = State after FF or FR
BB = EB . X1
BC = EC . X30
BD = ED . X60
BE = EE . X120
BF = EF . (FF + FR)

Ea, EB, EC, ED, EE and EF equals voltages applied to the emitter follower Q1 to provide current flow through the motor used for braking.

The schematic shown in FIG. 2A includes the emitter follower Q1 driving either motor M103 or M104 as controlled by the relay K3. A rapid braking of the tape occurs when the Stop control amplifier L10 provides current drive to the emitter follower Q1 through diodes CR2 and resistor R1. A capacitor C1 delays this current drive to make the braking smooth and to prevent stretching and breaking of the tape. The amplifier L10 also controls a discharge of the capacitor C1 through the transistor Q2 during any other mode other than the Stop mode so that the Stop mode can be successively repeated. A zenor diode CR3 limits the maximum current during the Stop control.

The brake control logic blocks L11 through L14 are electronic switches which are controlled from the tape-deck speed outputs so as to provide various levels of current to the emitter follower Q1. The reel size switch S1 also controls current level and therefore brake value by switching to a plurality of resistive levels R1, R2 and R3. During the Stop mode or Fast Forward or Fast Reverse modes, the diode CR4 pulls the diode CR1 to a minus voltage such as minus 24 volts and thereby disconnects the speed input and reel size inputs from the emitter follower Q1. During the Play and X1 modes the diode CR4 is back biased to thereby allow the speed input data to go directly to the emitter follower Q1 and control the braking levels of the motors M103 and M104.

Figure 6:
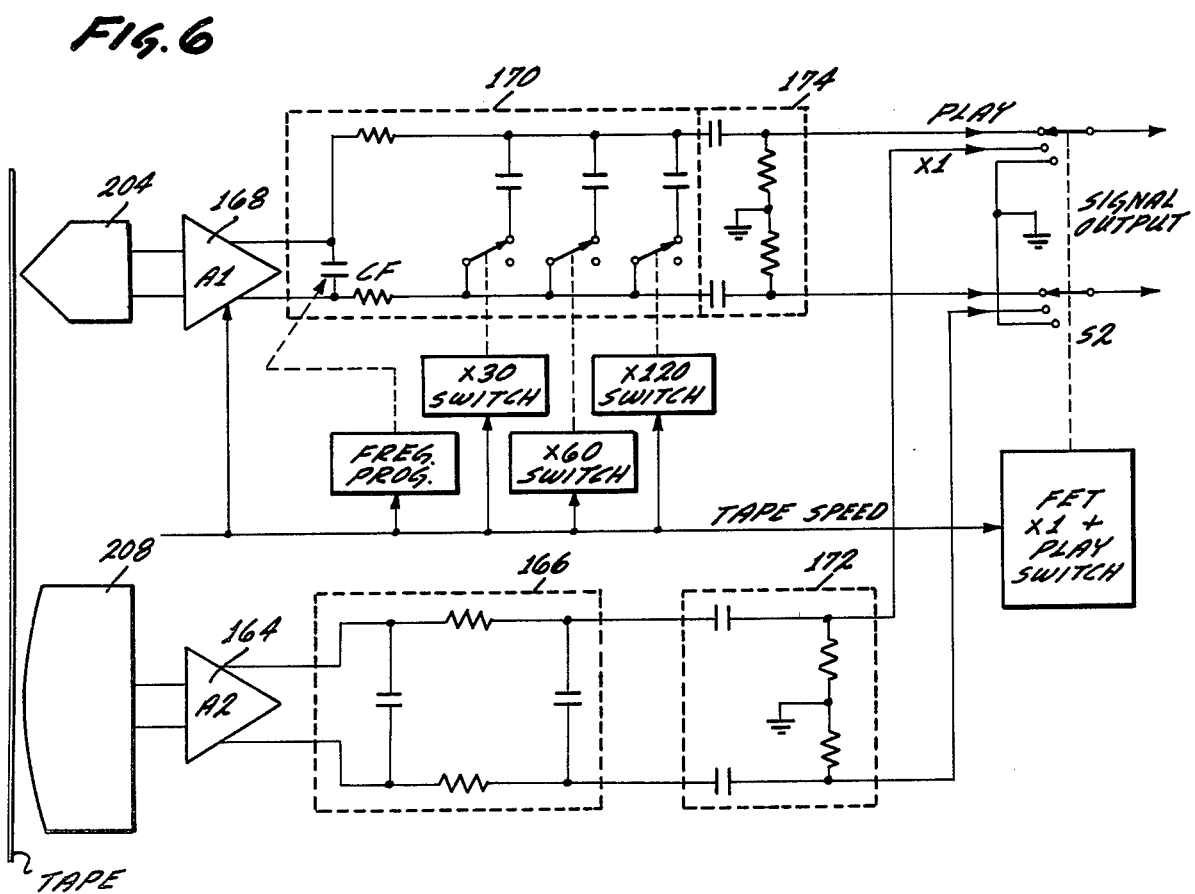
FIG. 6 illustrates a schematic of the compensated head amplifiers for playback in real time and at multiple high speed playbacks.

The tape head and amplifiers shown in FIG. 2 and in more detail in FIGS. 4, 5 and 6, provide accurate and stable reproduction of the dual track recorded signals with recorded frequencies from approximately DC to 100 hertz. The basic recording to be reproduced is made from a standard portable recorder operating at ⅛ inch per second and the recording is directly on the tape without the use of a subcarrier. This type of recording provides for extremely small reels of tape recording for long periods of time, such as 24 hours.

The ECG computer of the present invention provides for analysis of this recorded tape and requires that signals from the recorded tape be played back at real time (X1) or at increased playback speeds of X30, X60 or X120. Since the tape transport system allows for the speed of the tape to be switched between any of the four playback speeds, the output signal must have the same equivalent signal bandwidth for all playback speeds. The output signal must also be stable in gain and base line, and be free from transient switching artifacts.

As indicated above, the recorded signals have a frequency bandwidth of approximately DC to 100 HZ. and the amplifier system must reproduce these signals at any speed. This provides for equivalent frequency bandwidths of DC to 100 HZ. at X1, DC to 3,000 HZ. at X30, DC to 6,000 HZ. at X60, and DC to 12,000 HZ. at X120. Playback heads which are currently available do not provide for the reproduction of DC without the use of a subcarrier for the recorded signal or without the use of a magnetic flux head such as the Hall head.

The use of a subcarrier technique has several disadvantages since the tape must be increased in speed five to ten times to give an equivalent bandwidth over a direct recording technique. This increase in speed, of course, consumes extra tape which either increases recorder size or decreases recorder playing time. Also at the increased speeds, signal drop-outs of the subcarrier exist which would cause noise and would increase maintenance problems. In addition, signal distortions exist in the signal since the subcarrier must be filtered out and these distortions prevent an accurate analysis of the complex ECG signals.

The magnetic flux head or Hall head present other disadvantages which limit the use of this type of head. For example, this type of head has poor high frequency response due to gap construction and an inherent noise due to the flowing of DC current through an unstable semiconductor. In addition, since the Hall head measures the magnetic flux directly, this type of head is very susceptible to stray 60 HZ. fields and the tape transport includes several motors and a power transformer, all of which may emit large magnetic fields.

The present invention overcomes these difficulties by using the standard type of reproducing head, but constructed in a particular way so as to reproduce signals from the tape between 0.05 HZ. to 100 HZ. The use of the standard type of head, but with a novel construction must be associated with amplifiers, filters, and integrators so as to satisfactorily operate in the dual channel mode and at speeds of X1, X30, X60 and X120. As shown in FIG. 2, the present invention uses a separate head for the X1 reproduction of the recorded signals, and a separate head for the reproduction of the recorded signals at the higher playback speeds. The X1 playback head must operate to reproduce the recorded information, at a playback speed of ⅛ inch per second, which is equal to 125 millinches per second. With a signal frequency of 100 HZ., a wavelength on the recorded tape would consume a space on the tape of 1.25 millinches. The head may have a playback gap of approximately 0.1 millinches so that the head may be used satisfactorily at frequencies of 100 HZ. at the reproducing speed of ⅛ inch per second.

In order to reproduce the frequencies down to 0.05 HZ., the output signal must pass through an integrator so that the output signal appears flat in frequency response from 0.05 to 100 HZ. If the integrator rolls off 3 DBs at 0.05 HZ., then the integrator will roll off an additional 66 DB at 100 HZ. relative to the roll-off at 0.05 HZ. Any stray signals that may be picked up by the head, such as the 60 HZ. magnetic fields produced by the motors, are attenuated approximately 60 DB so as to essentially eliminate these stray signals. The head used in reproducing the information at the X1 playback speed does not produce self-generated noise because it is made of copper wire which is extremely stable.

Referring now to FIGS. 4 and 5, the particular details of the X1 head are shown and the design of the head is massive in size. For example, a typical length of the pole faces may be three to five inches so that the pole length at the lowest frequencies are longer than one wavelength. A pair of pole members 150 and 152 are separated from each other by a shield member 154 which has a Z configuration. The pole members include gaps 156 and 158 to provide reproduction of information from the dual track magnetic tape. The pole members support winding cores 160 and 162, and as can be seen in FIGS. 4 and 5, these winding cores are offset from each other so that both poles would be within a tape width of one-quarter inch since generally one-quarter inch width tape is used for recording. The Z shield 154 eliminates cross talk between the two channels and has a particular Z configuration due to the offset between the winding cores 160 and 162. The length of the laminated pole portions that hold the winding cores 160 and 162 must be sufficiently long so as to hold all the wire required to amplify the signals when the tape is moved at the low tape speed. The winding cores have a large number of turns, such as 25,000 turns, in order to provide for the reproduction of the recorded signals.

The output from the winding cores is applied to a sensitive amplifier 164, as shown in FIG. 6, and the amplifier is followed by the 66 DB integrator 166. The loss from the integrator 166 must be made up by the amplifier 164 in order to insure a sufficient output signal from the integrator.

A separate high speed head 204 is used for the reproduction at X30, X60 and X120 playback speeds. This high speed head 204 may be a conventional stereo playback head which has a frequency response of 3 to 12,000 HZ. The frequency response necessary for the X30 playback, which is equivalent to 3 and ¾ inches per second is 3 to 3,000 HZ. The frequency response at the X60 playback, which is equivalent to 7½ inches per second, is 6 to 6,000 HZ. and the frequency response for the X120 playback, which is equivalent to 15 inches per second, is 12 to 12,000 HZ.

The high speed head 204 shown in FIG. 6 supplies its output signals to the high speed amplifier 168 which is a DC amplifier having a response from DC to 15,000 HZ. This amplifier has its gain programmed in accordance with the tape speed signal provided from the system of FIG. 2. The output from the amplifier 168 is coupled to a programmed integrator 170 which integrates the output signal to give a flat response from 3 to 12,000 HZ. As shown in FIG. 6, a plurality of switches control the integrator 170 in accordance with the tape speed and a frequency programmer controls the frequency response of the integrator in accordance with the tape speed. Typically, the amplifier 168 is programmed for gain for the different gain outputs from the head at the three tape speeds. Frequency programming of the integrator 170 for the three tape speeds in the ratio of 1, 2 and 4 for the speeds of X30, X60 and X120 is accomplished by switching the value of the capacitor CF. The value of the integrating circuit 170 may also be switched in the ratio of 1, 2 and 4 to control the integrating time constant at the different speeds.

The integrators 166 and 170 are placed at the output of the amplifiers 164 and 168 to insure that all noise picked up from the heads or amplifiers is then attenuated by these integrators. This will give an extremely noise-free output without any 60 HZ. interference. The output from the integrators 166 and 170 are connected to high pass filters 172 and 174 so as to remove any DC component which may have been provided by the amplifiers 164 and 168. The output from the high pass filters 172 and 174 may then be switched using the switch S2, and the switch S2 may be an FET electronic switch so as to provide a transient free base line to insure that all subsequent components in the system are not disturbed. As indicated above, the switch S2 may be an electronic FET switch which may be digitally controlled in accordance with the tape speed so as to provide switching between several modes. These modes may be the X1 playback speed mode, the high speed mode, and a switching to ground mode. For example, during Fast Forward, Fast Reverse, or Stop, the amplifier output is switched to ground to prevent any transient signals from showing on the output.

As indicated above, and as shown in FIGS. 2 and 6, the tape transport uses two playback heads 204 and 208 to achieve the real time playback at X1 and the high speed playback at X30, X60 and X120 times recorded time. In addition to the use of two playback heads to achieve optimum fidelity to the recorded signal for the various playback speeds as explained above, the use of two heads also allows for the viewing of the ECG signals at high speed in a superimposed display on the oscilloscope 10 and a subsequent slowdown to the X1 speed to provide a paper writeout on the paper writer 12 of the same information previously viewed on the oscilloscope. FIG. 7 illustrates the tape loop including an adjustable time delay loop portion to allow for the operator of the ECG scanner to provide for the proper paper writeout in accordance with the previous high speed viewing and in accordance with the reaction time of the operator.

The paper writeout in real time after viewing at high speed is possible since the direction of tape flow is from right to left. Specifically, the magnetic tape from the supply reel 200 is guided by a plurality of tape guides to pass over a trigger head 202 and the high speed head 204. The tape is then guided by guide members to a variable delay loop portion 206. The tape is then guided by guide members to pass over the X1 head 208 and around the optical encoder pulley 100 to be received by the take-up reel 210. The variable delay loop 206 is used to vary the time before the tape is received at the X1 head 208 after being viewed by the high speed 204. The delay loop 206 provides a variation in time from a minimum to a maximum value in accordance with the position of the variable delay loop. The delay loop 206 includes a guide roller 212 which can be adjusted along a vertical path in accordance with the movement of the guide roller by a guide arm 214. A clamping knob 216 is used to clamp the arm 214 and roller 212 in the desired position. A pointer member 218 extends from the guide arm 214 to give a visual reading of the time delay.

The adjustment of the position of the guide roller 212 is variable to enable different operators to adjust the quantity of ECG signals that are written out prior to the desired portion and also the compensate for differences in operator reaction time. For example, the operator may be operating the Electrocardioscanner at X120 playback speed and may be viewing the superimposed image on the oscilloscope. The operator can see a single abnormal ECG beat, such as a PVC, since this will produce a characteristic visual and audio deviation from the normal superimposed image. Without hesitation, the operator presses the desired auto ECG key to change the speed to real time and to activate the paper writer. Because of the delay loop, the ECG complex having the PVC and some previous quantity of ECG complexes will be written out by the paper writer.

Since different operators may desire to view the superimposed image at different ones of the high playback speeds, such as either the X30, X60 or X120 speeds, the time required for the tape to move from the high speed head 204 to the real time head 208 varies in accordance with the speed of playback. Specifically, the delay time varies from 2 seconds to .5 seconds at the different speeds with the variable guide member 212 adjusted to provide for the minimum delay loop. The delay loop 206 when adjusted at its maximum position doubles the times before the tape passes from the high speed head 204 to the real time head 208. It is to be appreciated that when the operator switches from high speed playback to low speed playback, the tape movement is quickly reduced, so that the actual time before the tape previously viewed at high speed reaches the low speed head 208 is considerably in excess of the time periods given above. For example, if the tape speed could be instantaneously reduced to real time after the tape has passed by the high speed head 204, the minimum time the tape would take to get to the real time head 208 would be approximately 60 seconds. The variable delay loop means when adjusted to its maximum position doubles the time to 120 seconds. This allows the operator to write out a significant quantity of the ECG complexes prior to the irregularity, so as to help in the analysis of the medical problem. Since the onset of the irregular ECG beat may in itself contain valuable information.

The use of the variable delay loop 206 is important since the operator does not have to rewind the tape to write out a complex that he has already reviewed. As indicated above, the delay loop 206 also allows for different operator reaction times and these times would be different for different operators and would be different for the same operator as his proficiency changes due to training and experience.

The method of scanning at high speed and superimposing ECG complexes on an oscilloscope has been described above with reference to U.S. Pat. Nos. 3,215,136 and 3,718,722 which have issued on the dual track method and the single track method. The present application, although using a single track trigger technique provides for the triggering in a multispeed tape transport and provides a visual presentation on an oscilloscope 10 which is considerably improved over the prior art methods. The superimposed ECG presentation on the oscilloscope may be achieved using a trigger signal from the trigger head 202 which starts the cathode-ray tube trace before the P wave portion of the ECG complex. The position where the waveform starts relative to the start of the trace is variable to allow viewer preference or to make up for any inaccuracies associated with the trigger system. In addition, since the playback system operates at speeds of X30, X60, and X120, the time between the ECG complexes will vary with the playback speed. In order to insure that the complex does not change in shape or duration, the display time base speed varies with the tape speed. The time delay at the beginning of the trace also varies with playback speed to insure that the overall ECG complex remains superimposed with changes in tape speed.

FIG. 8 illustrates the position of the trigger head 202 relative to the playback head 204. The trigger head 202 is used to provide an oscilloscipe trigger signal from the ECG complex so that complete ECG complexes may be viewed starting with the P wave portion of the ECG complex. In actuality, the trigger signal originates from the R wave portion of the ECG complex which occurs later in time relative to the P wave portion. This general system is described in detail in above-referenced U.S. Pat. No. 3,718,772 and reference is made to this patent for full details.

Figure 9:
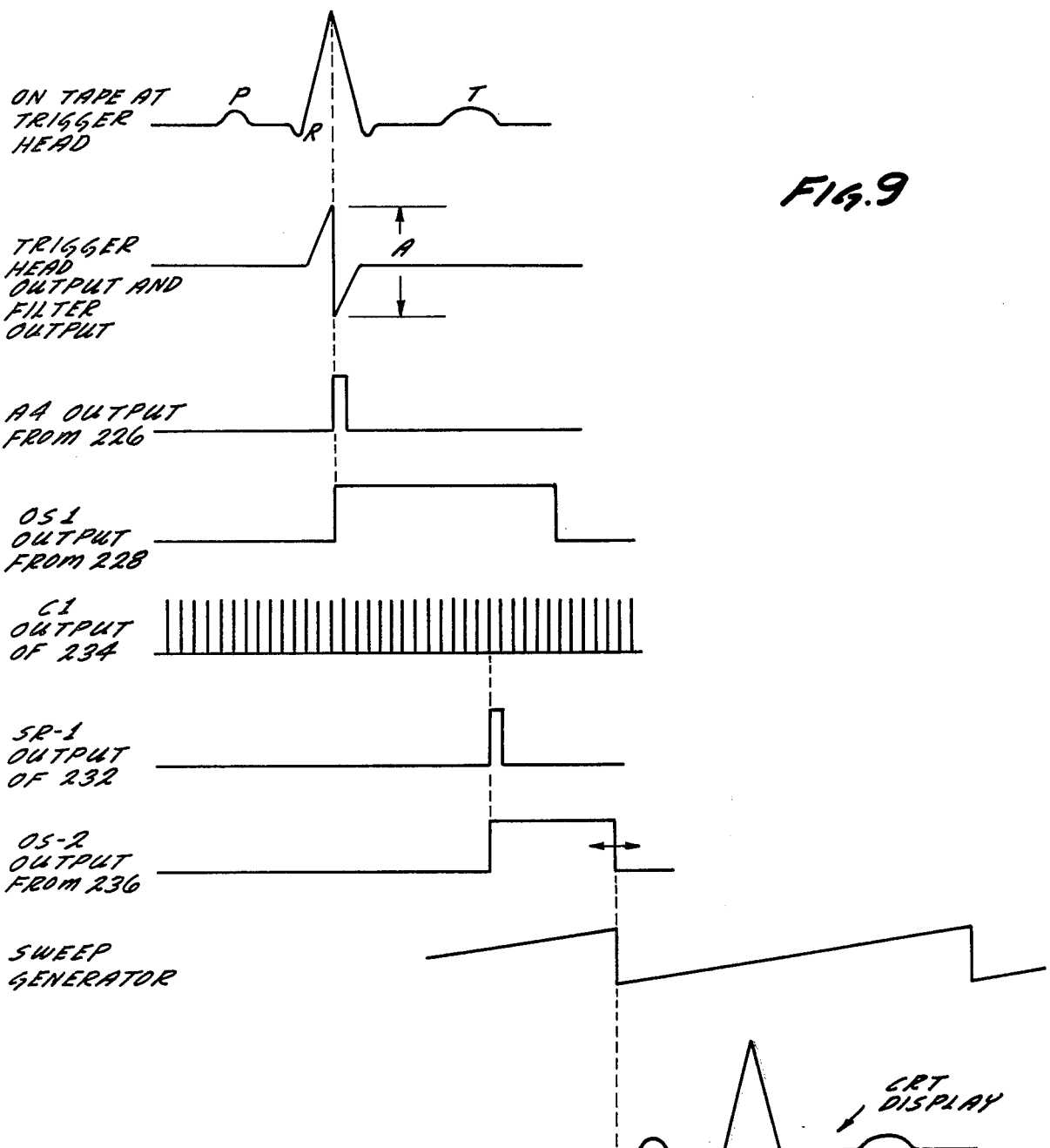
FIG. 9 is a series of waveforms used in explaining the tapedeck trigger system.
Figure 12:
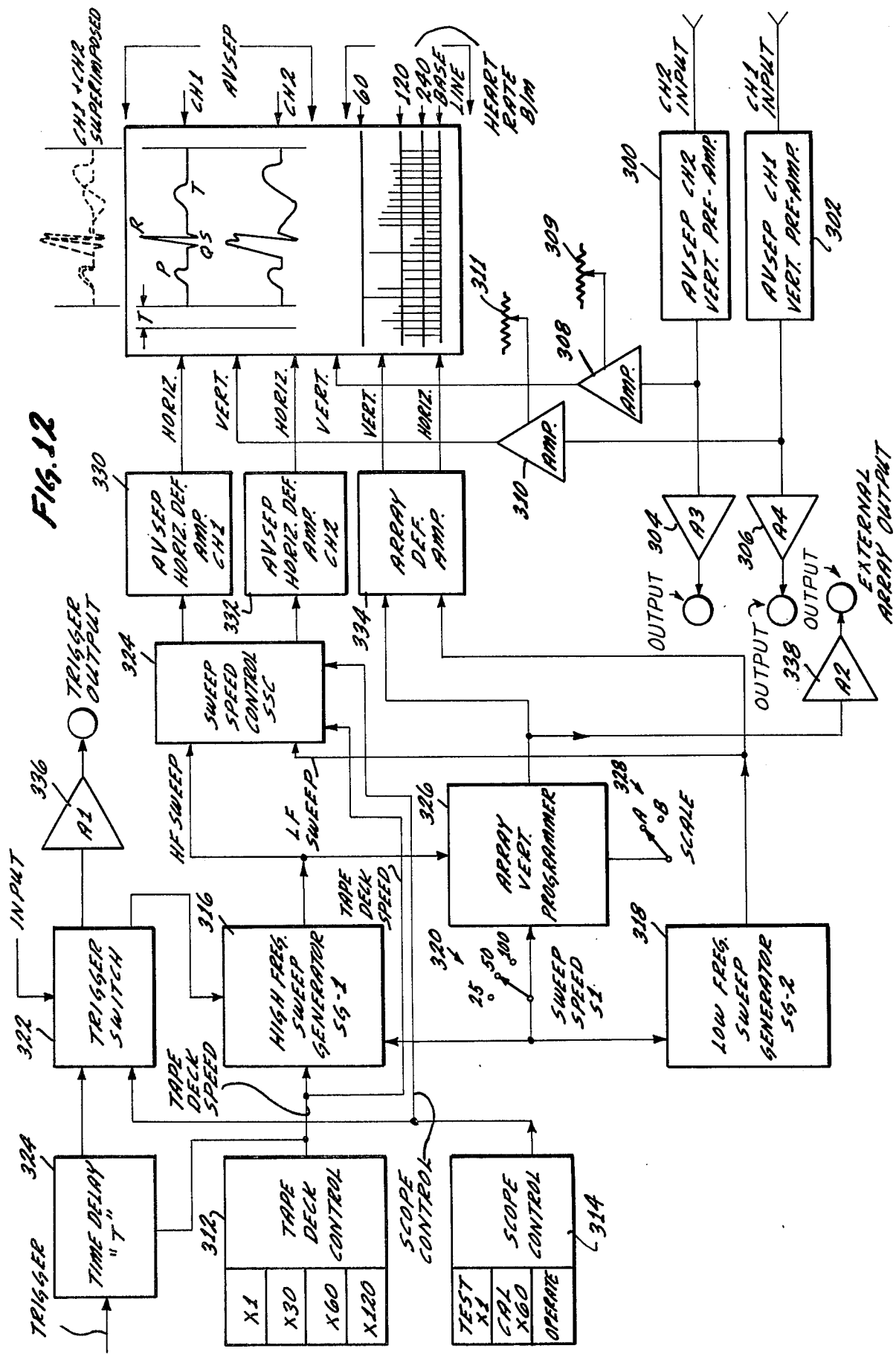
FIG. 12 is a block diagram of the multiscan oscillograph display including the drive system.

A typical superimposed ECG signal is shown in FIG. 12, assuming that the trigger signal from the trigger head 202 is able to start the sweep ahead of the P wave portion of each ECG complex. Referring to FIG. 8, the output from the trigger head 202 is typically as shown in FIG. 9, and is essentially the R wave portion of the ECG complex as differentiated by the head 202. This differentiated signal is referred to as A, and the amplitude of the A signal is directly proportional to tape speed. A typical ECG complex and the waveforms provided from the trigger system of FIG. 8 are shown in FIG. 9.

The ECG signals typically recorded from the heart in a moving patient, which is generally the case with the present invention, generally are noisy with artifact and these must be filtered before any further use. The filters are shown in FIG. 8 as part of blocks 220, 222 and 224 and there is a separate filter for each different speed to provide optimum artifact rejection at the different tape speeds. The filtering may be combined with amplification and with the blocks 220, 222 and 224 representing filter amplifiers controlled by a tape speed input to switch in the appropriate amplifier in accordance with tape speed. The amplifiers 224, 222 and 220 change the gain by factors of ¼, ½ and 1 with the tape speeds of X120, X60 and X30.

The output from the amplifier filters is connected to an amplifier 226 which varies the trigger level of a one shot multivibrator 228 in accordance with an automatic gain control provided by an automatic gain control amplifier 230. The automatic gain control measures the peak R wave level from the appropriate one of the filter amplifiers and then adjusts the trigger level from the amplifier 226 to be slightly below this level so that all base line noise or large T wave portions of the ECG complex are removed. The tape transport speed also controls the output of the one shot 228 so as to provide a proper width pulse to a shift register 232. Since the present invention uses a multiple speed tape transport, the clock 234 has three output rates which would typically be slightly more than 7,500, 15,000 and 30,000 HZ. The output rate of the clock 234 is controlled by the tape speed input.

The shift register 232 may typically have 2,048 bits so that at a clock rate of 15,000 HZ., which relates to the X60 speed, the time required for a signal on the tape at the trigger head 202 to move to the high speed playback head 204 would be calculated as:

$$T = 2048/15,000 \text{ seconds}.$$

At the tape speed of 7.5 inches per second, which relates to the X60 speed, this provides a trigger head to playback head spacing of 2048/15000 × 7.5 = 1.024 inches which is indicated in FIG. 8. Therefore, an R wave signal, which is used to trigger the shift register 232, would provide a trigger signal at the output of the shift register 232 at the same instant that this same R wave would arrive at the playback head 204.

In order to correct this timing, so as to shift the trace so that the P wave portion is displayed ahead of the R wave, a slight increase of the clock frequency is used. For example, a typical shift at the X1 speed would be 240 milliseconds which is equivalent to 3 milliseconds at the X60 playback speed. The normal time required for a signal to move from the trigger head 202 to the playback head 204 with a spacing of 1.024 inches may be calculated as approximately 134 milliseconds. Therefore, the clock frequency is increased in the amount of 4 in 134 to achieve the desired shift so that the P wave shows ahead of the R wave.

In order to provide for a variation in the triggering, which would be under the control of the operator, a second one shot 236 is used before the application of the trigger signal to the cathode-ray tube deflection circuit. A variable resistor 238 which is controlled from the front panel, shown in FIG. 1, allows for the operator to control the adjustment of this delay. FIG. 9 illustrates the timing diagram for the production of the trigger signal showing the production of the sweep to control the cathode-ray tube display to provide for the complete display of the ECG complex on the oscilloscope 10 shown in FIG. 1.

In order to provide for a digital clock in accordance with the tape travel, a clock drive mechanism as shown in more detail in FIG. 10 is used. In FIG. 2 and in FIG. 7, the clock drive pulley 100 was shown to be part of the tape path and this pulley is maintained in constant engagement with the magnetic tape as provided by the tape tensioning features described above. The pulley 100 provides a drive to an optical encoder which in combination with the pulley provides for the basic clock drive. Since these mechanical elements are controlled by the movement of the magnetic tape, they are generally designed to be lightweight and to have a relatively low inertia.

A shaft member 240 is coupled from the drive pulley 100, and includes a slotted disc 242 positioned at the end of the shaft, so that the slotted disc 242 moves with movements of the drive pulley 100. The disc may have 24 slots per revolution and a movement of the magnetic tape is translated into a rotation of the disc 242. A pair of light sources 244 and 246 which may be LEDs provided light energy directed towards the disc and specifically to pass through the slots in the disc 242. A pair of light detectors such as photocells 248 and 250 detect light output from the light sources 244 and 246. The diameter of the pulley 100 is adjusted so that each ⅛ inch of tape travel causes a signal output from each of the photocells 248 and 250. In addition, the photocells are spaced apart so that one photocell produces an output signal 90° in phase ahead of the other so as to indicate the direction of tape travel. This can be shown in FIG. 10A where the output of photocell 248 is shown in solid line and the output of photocell 250 is shown in dotted line.

The output signals from the photocells 248 and 250 are applied to amplifiers 252 and 254, which may be conventional buffer gates, so as to provide for amplified square wave pulses to be directed to a time clock. Since an output signal for each ⅛ inch of travel is provided at real time playback, an output signal each second is provided to the digital clock. Referring now to FIG. 11 the output of the optical encoder and input to the digital clock is shown to be square wave pulses having a 90° phase shift.

The digital clock system, shown in FIG. 11, provides for a visual output clock as shown at position 16 in FIG. 1. In addition, the digital clock provides output information which is used in the paper writer section by printer mechanism 14 to provide for printout of the digital clock information. As indicated above, the optical encoder measures tape length in ⅛ inch units and the digital clock system converts this to changes in time of day either increasing or decreasing. This is accomplished at the various playback speeds in addition to the fast forward and fast reverse speeds. A plurality of preset inputs 256, 258, and 260 allow the presetting of each digit to any number so that the start time of the digital clock can be correlated to the start time of the recording which is to be analyzed.

The digital time clock keeps track of the recorded time on a twelve hour basis and provides visual time of day outputs as shown by indicators 262 through 268. In addition, a pair of output indicators 270 and 272 provide a visual indication of AM or PM so as to cover a full twenty-four-hour day.

The digital clock is operated in a bidirectional mode either counting up or down and controlled by an up-down logic gate 274 and with each input pulse proportional to one second. Logic gate 274 determines which signal A or B comes first and then actuates standard up-down counters to count in the proper direction. The digital clock also provides output BCD signals of each digit in sequence which relate to the visual indication and to the AM-PM. These output command signals may either be controlled from internal timing controls such as an event or a marker control, or from an external input. For example, at a particular event or at a particular preselected time, a printout of the time may be provided by the printer 14 on the paper. This printout would be a typical digital printout such as 11:59 AM.

In addition to the printout of time, the digital clock provides additional sequential information to be printed immediately after the printout of the time. For example, the arrhythmia computer provides digital information as to the number of PVCs and SVTs and in addition to the printout of time, the number of such PVCs and SVTs may be printed out. This typically occurs when the tape transport and display operates in the trend mode. The typical printout is as follows: 12:00 AM 032 060. The printing of the numerals after 12:00 AM occurs sequentially, one at a time, after the AM has been printed.

The three numbers represented by 032 indicate the number of PVC beats and the three numbers represented by 060 indicate the number of SVT beats. Both of these numbers are provided from the arrhythmia computer portion of the system and the time of printing is controlled by the digital clock.

As indicated above, the digital clock controls a printout by the paper writer of the time when operated in a trend mode. At that time, the paper is moved at a relatively slow speed. The paper writer may be of the heat stylus type and would use a heat stylus located in the upper portion of the paper writer 12 and as represented by heat styli 276 and 278 as shown in FIG. 1. The digital printer 14, shown in FIG. 1, has a mechanical separation from the heat styli 276 and 278 and because of this mechanical separation, the visiual printout would normally have time errors.

Specifically, since the digital printer is ahead of the writing styli, the writing styli provides the writing of information correlating to a particular time on the recorded tape and the digital printer is considerably ahead of the writing styli. At low paper speeds, such as in the trend mode, the time error is considerable. As an example, the separation between a print wheel, which is part of the digital printer 14, and the writing styli 276 and 278 may be on the order of 8 centimeters. At a paper speed of 1 millimeter per second, this would represent a time error of 80 minutes. The digital clock shown in FIG. 11 corrects for this time error for paper speeds of 1 millimeter per second or 2 millimeters per second, which correspond to the tape playback speeds of X60 or X120. Generally the tape playback speeds of X60 or X120 are the only ones used in the trend mode. Specifically, the correction for the time error is generated from the signals which are used to provide for the digital display.

During a trend printout, the time is digitally printed with this time correction of 80 minutes. When the data written by the styli 276 and 278 gets to the area of the printer 14, the correct time is then printed along the edge of the paper. The method of achieving this printout is greatly simplified in that only one set of components is used to drive the digital display and then this same BCD data as displayed is modified to provide a correct printout of the time.

As shown in FIG. 11, the up-down control 274 is driven by the output pulses from the optical encoder which correspond to a one-second rate for each ⅛ inch of tape. Depending on the direction of tape travel, one of the pulses always leads the other, so as to provide for the up-down control producing the appropriate output pulses to drive the dividers 280 through 286 and the drive 288, which controls the AM-PM indication.

The display indicators 262 through 272 may be standard LED or Nixie tubes and displays four numbers such as 11:59 to indicate the time and also the AM-PM indication. Since the output of the up-down control 274 corresponds to a one-second rate, the first divider 280 divides by 60 to change the one-second rate to minutes and to drive first display 268. The succeeding logic dividers 282, 284 and 286, convert the minutes to tens of minutes by dividing by ten, to hours by dividing by six and to tens of hours by dividing by 10. Finally, the divider logic 288 provides an output indication of AM or PM at 12 o'clock.

The first three least significant digits may be changed any time by controls 256, 258 and 260, so as to initially set the indicators and dividers to a desired time which corresponds to the start time of recording on the recorded tape. The most significant digit is controlled by the set switch 256, so that this set switch not only sets its own indicator 264, but at the change from 9 to 0, the most significant digit is changed from 0 to 1, and when the displays 264 and 262 go from 11 to 12, the AM-PM lamps are also activated.

During the X1 playback mode, the digital time is normally printed on the paper writer by the unit 14 from either an external push button command or at the actual start of the paper writer. These two inputs are shown provided to the data selector multiplexer 290 which includes counters and gates to look at each BCD number in sequence, one at a time. In the X1 playback mode, the actual time of day from the clock output drivers 280 through 286 are connected to a latch multiplexer 292 via the printer trend mode correction unit 294. The latch 292 is formed of flip-flops to hold the digital value of the display in BCD form. The unit 294 is formed from gates which are sampled by the clock 296 and then outputted into the latch 294. The paper speed from the trend or X1 signals is inputted to control the take off point, with the correction of 80 minutes when desired. The printer trend mode correction is controlled during the X1 playback mode to merely pass on the clock outputs to the latch multiplexer 292. The data from the latch 292 and multiplexer 290 is multiplexed out in sequence at a rate determined by the data sequence clock 296. The clock 296 is of standard design having an output pulse rate controlled by the speed of the paper writer so as to output the printer at a slow rate on trend or at the faster rates of 25 or 50 mm/s on X1.

In the X1 operate mode, the paper writer is driven at a relatively high speed and the time differential between the writing of the data by the heat styli 276 and 278 and the time printout by the unit 14 is relatively small. This time error is on the order of 4 to 5 seconds and no time correction may be necessary in this mode. It is to be appreciated, however, if such a time correction is desired, it could be provided by conventional means by using a time delay in the printout of the information. The output from the multiplexer 290 is BCD data, and this data is coupled through a BCD interface 298 to the external digital printer 14, where generally one digit at a time is printed. The print commands to the printer 14, which correlate to the BCD data, is supplied by the data sequence clock 296. In addition, print inhibit signals are supplied to and from the data sequence clock. During the X1 playback mode the data sequence clock is reset to start over, after the AM or PM is printed.

With the exception of the time of printing by the digital printer 14, the digital time clock operates the same as the X1 speed and at faster tape transport speeds. During X60 or X120 trend, analysis of the ECG complexes is provided and output signals reflecting this analysis as a trend is written by the paper writer. This output trend data consists of analog heart rate, analog ST level, event marks and the digital printout of time and number of PVCs and SVTs, both of which are determined by the arrhythmia computer. As described above, a time correction must be made during the trend mode to correct for the mechanical spacing between the heat stylus and the digital printer. Specifically, the time that is printed by the digital printer 14 during the trend writeouts is corrected by one hour and twenty minutes. This enables the heat stylus writeout to proceed to provide writeout with the paper moving at a slow rate and with the correct time printed along the paper edge.

Figure 13:
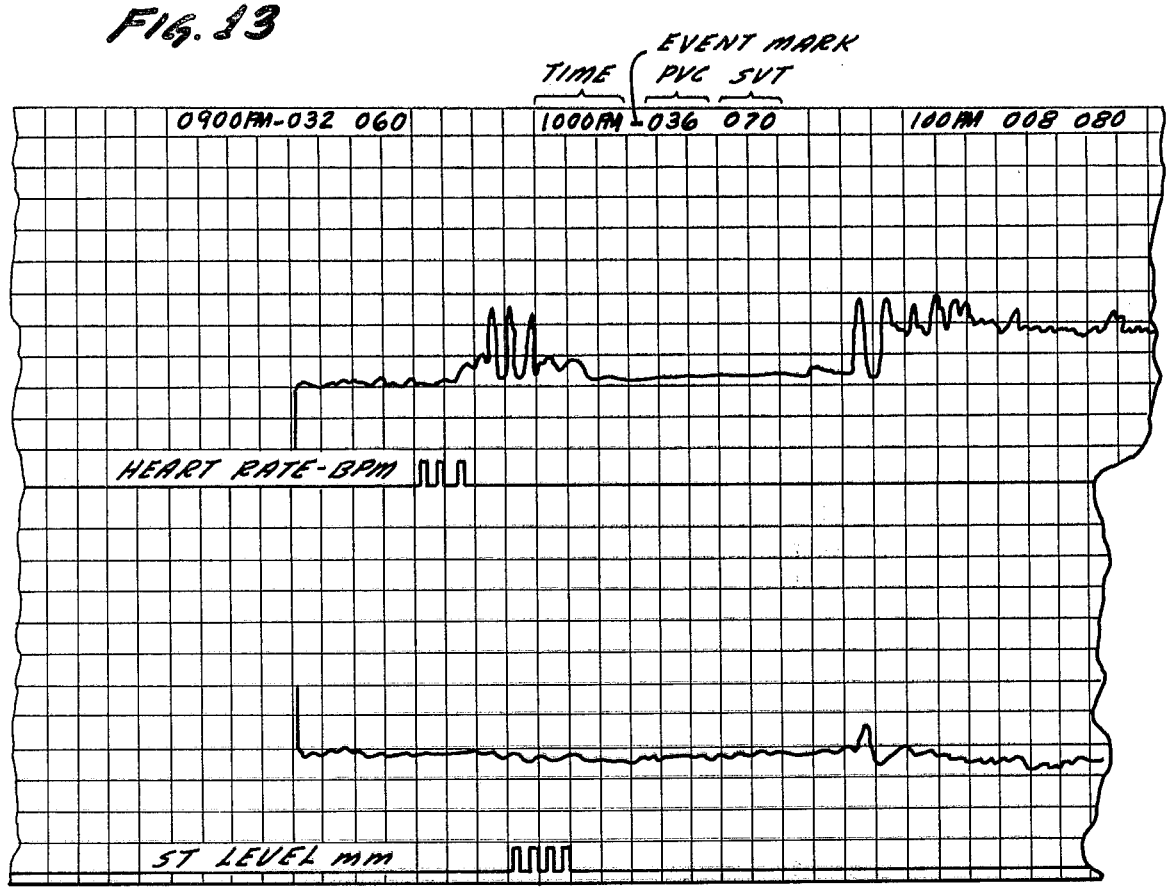
FIG. 13 illustrates a typical trend chart writeout including event markers and digital information.

In order to provide this time correction of 1 hour and 20 minutes, the printer trend mode correction unit 294 provides the following operation. The input data proceeds into the unit 294 until the two least significant bits reach 59. After 59 is changed to 00 in the unit 294, but before the next hour digit is changed, the clock data from the unit 294 is sequenced at a high rate into the latch 292 and is then inhibited from further change for an hour. The latch 292 therefore receives the time as 11:00 AM, rather than 12:00 as displayed by the display elements 262 through 268. A twenty minute delay in printing is then initiated by waiting until a 2 occurs in the second least significant digit, such as at 12:20 AM on the digital display, before the printer 14 is commanded to printout the information held in the latch 292 which would be 11:00 AM. The printing of the time is then followed by an event mark as shown in FIG. 13.

After the event mark, the arrhythmia computer output would supply information to be printed at positions following the time as explained above. The output circuitry of the arrhythmia computer is connected in parallel with the digital time clock to supply information to the digital printer. The data sequence clock 296 is used to control the sequential printing from the arrhythmia computer of the information supplied by the arrhythmia computer.

The oscilloscope display system to provide display on the CRT tube face 10 is shown in FIG. 12. The oscilloscope display consists of the CRT 10 having three independent channels to show the ECG complexes or other data. The unit operates generally in two modes so that at the X1 speed, two of the channels show ECG complexes and the third channel is inactive. In the other mode of operation, which is for high speed analysis at either X30, X60 or X120, the display consists of three channels. Specifically, two channels provide the ECG information with each in superimposed presentation which has come to be known as AVSEP and a vertical bar presentation which is known as an arrhythmia bar graph. The arrhythmia bar graph represents the time interval between heartbeats.

The particular AVSEP display of the present invention provides for a high speed analysis so that the operator may view and analyze two leads of ECG data in a compact viewing area and in the same display the heart arrhythmia may be viewed by observing the arrhythmia vertical bar graph. The three channel display is shown in FIG. 12 and includes the channel 1 and channel 2 display of AVSEP information and the third channel which represents the arrhythmia bar graph display.

The channel 1 and channel 2 displays will be from different sets of ECG leads which were previously connected to the patient. The complexes of each channel are superimposed on top of each other at a rate of X30, X60 or X120 times the real time. This provides a flicker-free presentation for normal heart rates. Since the ECG data from each set of leads may be different, the operator may provide analysis by a comparison of the two channels at the high speeds. In addition, the channel 1 and channel 2 information may be superimposed on top of each other so as to provide for superimposition of the superimposed information which allows for a rapid determination of variations between the data from two channels. Whether the information is displayed as shown in block 10 in FIG. 12 or superimposed on each other, and shown in dotted form above block 10, this multiscan approach allows determinations of different PR intervals, R waveform shape, or ST slope which are examples of the changes that may exist between different sets of ECG leads.

As shown in FIG. 12, a delay time T may be varied so as to delay the trigger input to the start of the trace. This delay has been described with reference to FIG. 8 and 9. The horizontal time scales for the AVSEP display may be expanded to show equivalent speeds of 25, 50 or 100 millimeters per second of real time display. In addition, vertical expansion allows displays of 5, 10 and 20 millimeters per millivolt recorded information. As indicated above, vertical controls allow the superimposition of both complexes on top of each other so that a direct comparison of the different ECG complexes may be accomplished. For example, the ST slope may exhibit changes from different ECG leads which may give important diagnostic data.

The horizontal time base expansion to provide pre-calibrated sweeps speeds equivalent to 25, 50 or 100 millimeters per second must also be compensated for changes in the playback speed of X30, X60 and X120. In addition, the trigger delay circuit which provides the variable delay of T as shown in FIG. 12 must also be compensated in accordance with changes in speed of the tape transport.

The arrhythmia bar presentation includes a single switch 328 to change the vertical bar height 2 to 1 to provide either a scale A or scale B. The horizontal sweep speed of the arrhythmia bar trace may also be varied during the AVSEP trace horizontal expansion to allow more or less packing of the vertical bars. The number of bars per sweep may be multiplied by the ratios 25, 50 or 100 to correspond to the time base expansion. Changing the tapedeck speed will also vary the sweep speed for the arrhythmia bar graph in the ratio of 30, 60 or 120. These variations in sweep speed for the arrhythmia bar presentation may be used to show more or less detail in the arrhythmia pattern by compressing or expanding the space between the bars.

Generally, the features described above are for use of the oscilloscope display 10 when operating to provide high speed analysis. When operating in the X1 mode, the system of FIG. 12 allows real time sweep speeds of 25, 50 or 100 millimeters per second under a manual control or under tapedeck control. The tapedeck control will automatically change the display from an AVSEP presentation when operating at X30, X60 and X120 to a normal X1 sweep when the tapedeck is controlled to operate at the X1 speed. The change from one mode to another is calibrated so as to eliminate any need for adjusting the horizontal and vertical controls.

The oscilloscope display 10 is provided from ECG signal preamplifiers 300 and 302 which amplify the signal from the tapedeck to a suitable level for display and for distribution through output amplifiers 304 and 306 to other portions of the system. The output from the preamplifiers 300 and 302 are coupled through vertical deflection amplifiers 308 and 310 to the vertical inputs of the oscilloscope. Variable potentiometers 309 and 311 allow adjustment of the vertical traces on the oscilloscope 10 to provide a separate display of the two channels of information of a superimposition of the two channels as shown by the dotted portion of the drawings.

The series of push buttons shown in block 312 control the speed of the tapedeck from front panel portion 60 shown in FIG. 1, and also provide tapedeck speed inputs to the system of FIG. 12. The series of push buttons shown by block 314 from front panel portion 64, control the traces on the oscilloscope and provide inputs to the system shown in FIG. 12.

Two sweep generators 316 and 318 generate saw-tooth output signals to provide a constant sweep presentation for the various operating conditions. The high frequency sweep generator 316 operates in conjunction with the tape speeds of X30, X60 and X120. In addition, a control switch 320 provides control of the time bases of 25, 50 and 100 millimeters per second. The combination of the three time bases and the three tape transport speeds would give nine combinations, but it can be seen that this may be simplified to a total of five sweep speeds, which are as follows: X30 and 25 millimeters per second, X30 and 50 millimeters per second, or X60 and 25 millimeters per second, X30 and 100 millimeters per second, X60 and 100 millimeters per second or X120 and 50 millimeters per second, and X120 and 100 millimeters per second. The low frequency sweep generator 318 is digitally controlled to generate three different slope saw-tooth waves, to provide the time bases of 25, 50, or 100 millimeters per second in accordance with the position of the switch 320. The output from the low frequency sweep generator 318 is used to provide the arrhythmia bar graph time base and, in the X1 tape transport speed or in the test X1 mode, the low frequency sweep generator 318 is used to provide the sweep for the ECG complexes displayed on the oscilloscope display 10. The low frequency sweep generator 318, when used in a calibrating mode, does not receive an external trigger, but is freerunning at 25, 50 or 100 millimeters per second.

The high frequency speed generator 316 is triggered either at a 60 HZ. rate or from the trigger circuit shown in FIG. 8 depending on the position of the control switches 314. For example, when the Cal X60 button is activated, 60 HZ. signals are used to trigger the high frequency sweep generator 316. When the Operate button is activated, then the trigger input is from the trigger delay circuit described in FIG. 8 and given the general designation 322 in this FIG. 12.

The output of the high frequency sweep generator, 316, is coupled to a sweep speed control switch 324 and also to an arrhythmia vertical programmer 326. The arrhythmia vertical program 326 is also controlled by the sweep speed switch 320, in addition to a scale switch 328. The output signals from the arrhythmia vertical programmer 326 are used for the vertical deflection for the arrhythmia display. The programmer 326 is a standard programmable amplifier which has its gain changed by digital inputs from the sweep speed switch 320 or the scale switch 328. The scale switch 328 controls the vertical deflection to be in one of two precalibrated signal levels.

The sweep speed control block 324 is a digitally controlled electronic switch which provides the proper horizontal sweep to the AVSEP horizontal sweep amplifiers 330 and 332. For example, the high frequency sweep provided by generator 316 and the low frequency sweep provided by generator 318 are both coupled to the sweep speed control 324 and the appropriate one of these sweeps is coupled to the sweep amplifiers 330 and 332 under the scope control and the tapedeck speed control during the tapedeck speeds of X30, X60 or X120. During tapedeck speed of X1, or when the scope control 314 is activated at test X1, the low frequency sweep is passed to the horizontal deflection amplifiers 330 and 332. The sweep speed switch 324 may consist of FET transistors connected to pass the proper one of the two sweeps to the deflection amplifiers 330 and 332. As indicated above the control of the FET switch 324 is by the tapedeck speed input or the scope push-button control.

The arrhythmia vertical programmer 326 receives the high frequency sweep signal from sweep generator 316 and provides the signal as an output to the arrhythmia deflection amplifier 334. The horizontal sweep of the arrhythmia deflection amplifier is controlled from the low frequency generator 318.

The deflection amplifiers 330, 332 and 334 are used to drive the three channel oscilloscope having display 10 in a conventional manner. The vertical deflection amplifiers 308 and 310 bring the tapedeck signal to a high level to drive the vertical deflection for these two channels. In addition to the output signals provided through amplifiers 304 and 306, the trigger output is provided through an amplifier 336 and the arrhythmia output is provided through an amplifier 338 to external outputs, and these amplifiers provide signals which may be used to drive external displays.

The two channel paper writer 12 shown in FIG. 1 has provision for writeout of two channels, using styli 276 and 278 in addition to the digital printout from digital printer 14. The writeout with the two channel styli 276 and 278 may be for either two channels of ECG signals reproduced in real time and with the paper moving at a relatively high speed, or for writeout of two channels of trend information with the paper moving at a relatively low speed. In addition to the two styli 276 and 278 to write out the dual channel information, three event markers, as shown at positions 400, 402 and 404 in FIG. 1 and FIG. 14, provide marker indications to indicate the occurrence of particular transient data.

As described above, the digital printer 14 is also used to print sequentially a series of numbers and AM or PM along one edge. FIG. 13 illustrates a typical two channel recording when the electrocardioscanner of the present invention is used to provide a trend chart. The trend chart in FIG. 13 shows the average heart rate in the upper portion of the chart and the ST level on the lower portion of the chart, all with relation to time. Along the upper edge of the chart the time is printed out on an hour-by-hour basis with an AM or PM indication, followed by a time marker produced by the event marker 400 shown in FIG. 14. The event marker is then followed by a three digit number representing the number of PVCs which have occurred in the next hour. This is followed by the number of SVTs which have occurred in the next hour. As previously described, the printing of the time is delayed for an 80 minute period to compensate for the time error in the movement of the paper, so it is possible to have the information relating to the PVCs and SVTs occurring in the next hour and to have this printed immediately following the time indication.

At a central position in the chart, the event marker 402 shown in FIG. 14 produces event marks which indicate that the PVCs have exceeded a predetermined number of PVCs per minute. This predetermined number is preset and is adjustable from the front panel of the electrocardioscanner by switch 46 shown in FIGS. 1 and 8. At the bottom edge of the chart, an event mark is produced by the event marker 404 and such an event mark indicates that the number of SVTs per minute have exceeded a preset value.

The heat styli 276 and 278 are controlled by galvanometers 406 and 408, and the input signals to drive these galvanometers come from the tapedeck. Specifically, the preamplifiers 300 and 302 shown in FIG. 12, provide drive for amplifiers 304 and 306 and the output from the amplifiers 304 and 306 are applied to switching amplifiers 410 and 412 shown in FIG. 14. These switching amplifiers 410 and 412 are digitally controlled and accept more than one input and provide output signals in accordance with the switching logic. For example, the trend input signals are also applied to the amplifiers 410 and 412. The control of the switching amplifiers 410 and 412 is provided by logic blocks 414 and 416, which include standard gate logic. The logic blocks 414 and 416 may be identical and consist of gates and flip-flops which output four logic states to control the gain of the programmable amplifier 410 to four different gains. The logic blocks 414 and 416 control the ECG sensitivity from the push button controls 36 and 38 when the printout is ECG complexes in real time. In addition, a trend input control signal is applied to the logic blocks 414 and 416. When the trend input control signal provides information that the trend program is to be printed, the gate logic 414 and 416 controls the amplifier switches 410 and 412 to provide as output signals, to the galvanometers 406 and 408, the trend signals.

The control of the paper drive is in accordance with the push buttons 40 and 62 shown in FIG. 14 and in FIG. 1. If the paper writer control section 62 is activated to control either ECG or auto-ECG, then the output speed is determined by the controls 40 as applied to digital logic circuit 418. The circuit 418 consists of standard gates and flip-flops to output three logic states. The logic circuit 418, in turn, provides control to digital logic circuit 420 to control the motor speed at three different values. The circuit 420, which consists of standard gates and flip-flops is also controlled by the four push buttons 62 to give a total of four different motor speeds and an event output state. A motor drive 422, which consists of relays, is driven by circuit 420 and in turn controls two motors 424 and 426, each at two speeds.

The combination of the particular speed from controls 40 and the ECG or auto-ECG selection from controls 62 provides a control of the motor drive 422 to control a motor 424 to drive the paper at the higher speeds. If the trend mode is selected from the group of push buttons 62, then the digital logic circuit 420, as modified by the X60 or X120 tapedeck speed, is used to control the motor drive 422 and ultimately the motor 426 at the appropriate speed in accordance with the tapedeck speed. Specifically, the motor 426 at a tapedeck speed of X60 would provide a paper drive of 1 millimeter per second. At the tapedeck speed of X120, the paper speed is 2 millimeters per second so as to keep the times scale on the trend chart of 1 millimeter equal to 1 minute. The paper drive speed using motor 424 is either 25 or 50 millimeters per second in accordance with the control provided by the keyboard buttons 40.

The digital logic circuit 420 provides a further control of an event marker when the button marked Event in the group of buttons 62 is activated. This, however, occurs only when the paper writer is in the ECG mode. Also, each time the tapedeck starts in the X1 mode, the digital logic circuit 420 provides an output to the event markers through the event stylus driver 428.

The paper writer also includes the digital printout mechanism 14 which is an one character impact printer that is sequentially activated in a conventional manner to print a series of numbers along the side of the paper. Input to this printer may be from the digital time clock as described above and from an arrhythmia computer to achieve the printout as shown in FIG. 13. The rate of printout is varied for the different paper speeds to provide a constant spacing between the characters. The digital printer is controlled by the printer electronics 430 which as indicated above, receives information from the digital time clock and from the arrhythmia computer.

Three event styli 400, 402 and 404 are driven from the event stylus driver 428 which receives two inputs from the arrhythmia computer to provide representation of PVS and SVT events, and also receives an event input from the digital control logic 420 as described above.

As shown in FIG. 13, the typical trend writeout provides a dual channel writeout of heart rate and ST level. The paper writer system as shown in FIG. 14 when controlled in the trend mode, provides such a trend chart. The heart rate channel may be calibrated with a heart rate scale from 0 to 250 beats per minute, and the ST channel may have a scale from −5 millimeters to +5 millimeters. These scales will generally cover all of the ranges encountered in ECG monitoring. The presentation of this dual channel trend information is coupled to the paper writer as shown in FIG. 14 and is specifically coupled into the switching amplifiers 410 and 412 and is controlled to provide output signals to the galvanometers 406 and 408 which in turn control the heat styli 276 and 278. The actual trend information is produced by two module sections 432 and 434 shown in FIGS. 1, 15 and 16.

FIG. 15 illustrates a block diagram of the heart rate trend computer section 434. The heart rate trend computer includes inputs relating to the two tape trend speeds of X60 and X120 so as to control the output signal for these two speeds. The trigger signal produced by the system of FIG. 8 is also provided as an input. This trigger signal was conditioned as described above to eliminate artifact noise. The trigger signal and the speed signals are applied as inputs to a pair of one shot multivibrators 436 and 438. These one shots generate a narrow pulse for each trigger input signal. The width of the output pulses from the one shots are adjusted to be in direct relation to the speed input. Only one output pulse from either of the one shots 436 and 438 is coupled to a low pass filter 440 depending upon the speed at which the tape transport is moving.

The low pass filter provides a pulse averaging of the input signal so that the output DC level of the low pass filter 440 is in a direct relationship to the input heart rate. The different pulse widths from the one shots 436 and 438 insure that the amplitude of the output signal from the filter 440 is related to heart rate and not playback speed. The switch 442 varies the filter time constant so that the output response time of the filter 440 may be varied over a range of beats before the change in rate is fully and accurately displayed on the trend chart. The output from the low pass filter 440 is passed through an amplifier 444 to bring the level of the DC signal to a sufficient level to drive the galvanometer 408 as shown in FIG. 14. A variable potentiometer 446 may be used to adjust the DC level so as to control the position of the DC trace.

FIG. 16 illustrates the block diagram of the ST level computer which provides an output signal to control the galvanometer 406 to provide a writeout of the ST level information. The ST level computer may be of the type described in patent application Ser. No. 271,548, filed on July 13, 1972, in the name of Donald Anderson and now abandoned, and reference is made to this Patent Application for a fuller description of the ST level computer. Generally, the input ECG signals from either the first or second channel is selected by a switch 448 for input to filter 450. The filter 450 is designed to provide particular frequency filtering in accordance with the tape speed of either X60 or X120 and these tape speed signals are shown applied to the input signal filter 450.

After the input ECG signal has been filtered, it is coupled to a sampling and level measuring circuit 452 which also receives the tape speed inputs. In addition, a sample time delay control 454 adjusts the ST sample point from 20 to 100 milliseconds after the start of the S wave. After a determination of the DC level of the ST segment by the sampling and level measuring circuit 452, this DC level is filtered by a low pass filter 456 which may have its time constant adjusted by a control 458 to change the response time between a minimum to a maximum number of beats. The output from the low pass filter 456 is applied to an ST level amplifier 460 which includes a zero adjust 462. The amplifier 460 provides an output signal to control the galvanometer 408 to provide for a writeout of the ST level on the trend chart.

Figure 17:
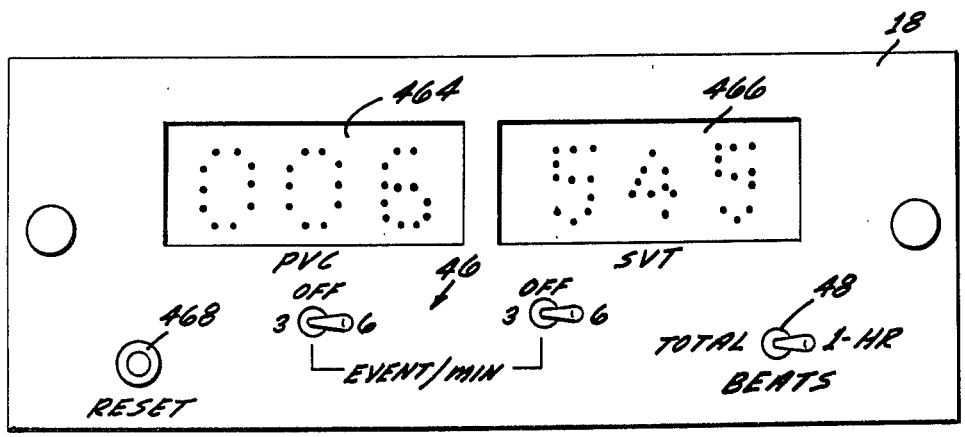
FIG. 17 illustrates the front panel of the arrhythmia analyzer.

The arrhythmia computer section of electrocardioscanner also provides information for display in the arrhythmia computer display portion 18 shown in FIG. 1 and shown in more detail in FIG. 17. The arrhythmia computer also provides output signals for use by the paper writer to control the digital writer 14 to provide numerical indication of arrhythmia information, and also to control event markers to provide information representative of arrhythmia information exceeding a preselected value. The front panel 18 includes two windows 464 and 466, each of which display numbers up to 999. The left window 464 displays a number of premature ventricular contracts (PVC). The right window 466 displays a number of supra-ventricular ectopic beats (SVT). Each display may be controlled by control switch 48 to totalize either in a one hour or on a cumulative basis. In addition, control of the event markers may be provided so that an output event mark is produced only when the number of PVCs or SVTs exceed predetermined selected number of such PVCs or SVTs. These are controlled by the switches designated 46. A reset button 468 controls all of the displays to return to zero.

The arrhythmia computer receives the input ECG data and displays the computed data on the front panel 18 shown in FIG. 17 and has the computed data digitally printed out on the trend chart as shown in FIG. 13. As described above, a typical trend chart shows the PVC and SVT information immediately following the time marker. In addition, the event markers at the middle and bottom edge of the trend chart paper provides event marks when the PVCs and SVTs exceed preselected numbers of events per minute.

FIG. 18 illustrates a block diagram of the arrhythmia computer. The input ECG data is coupled to a filter 470 which also receives speed signals from the tapedeck representing the trend speeds of X120 and X60. The speed data and the ECG data are coupled from the filter into the remaining portion of the arrhythmia computer and with the input speed data used to control timing functions, since the speed of the tapedeck would affect the timing of the signals. The output signals from the filter 470 are coupled to a plurality of comparator devices 472 through 480 which perform their comparisons in a conventional manner. Generally the comparators 472, 474 and 476 establish a plurality of criteria to determine if the ECG information contains a PVC. The comparator blocks 478 and 480 in combination with information from blocks 472 and 474 provide criteria that must be met to determine if the ECG information contains an SVT.

Figure 19:
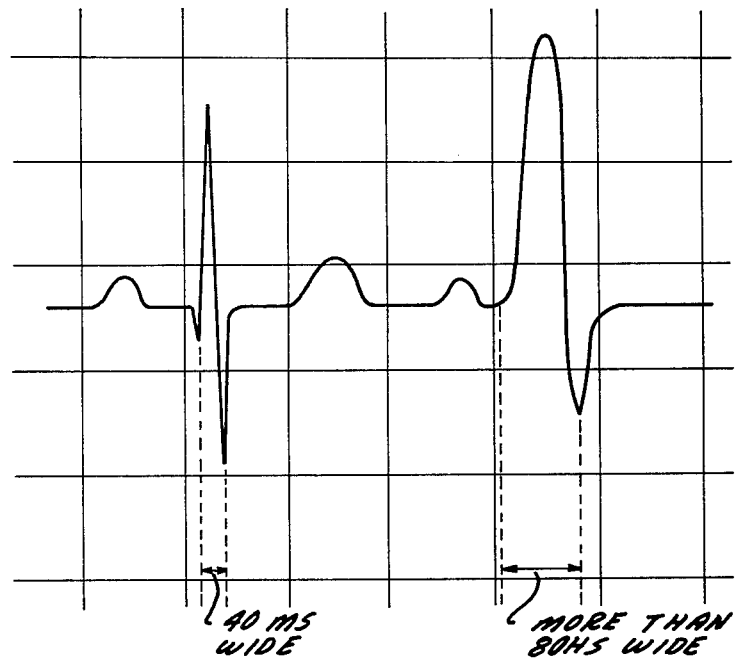
FIG. 19 illustrates a typical ECG complex as compared with an ECG complex with a wide QRS segment.

In order for the system of FIG. 18 to provide an output representing a PVC event, the ECG complex must meet the following criteria. The first criteria is shown in FIG. 19 and specifically, in order to be counted as a PVC, the QRS width must be greater than a predetermined width. For example, the QRS width must be greater than 80 milliseconds. This is shown in FIG. 19 where a normal ECG complex having a QRS width of approximately 40 milliseconds is followed by an abnormal ECG complex having a QRS width of greater than 80 milliseconds. The comparator 474 provides output signals representing whether the QRS segment is either wide or not wide. Comparator 474 may consist of an R wave width measuring circuit which is a flip-flop that is triggered as the R wave rises and reset as it falls. The time duration of this flip-flop is compared using standard gates against a time standard such as a one-shot which is triggered as the R wave rises.

Figure 20:
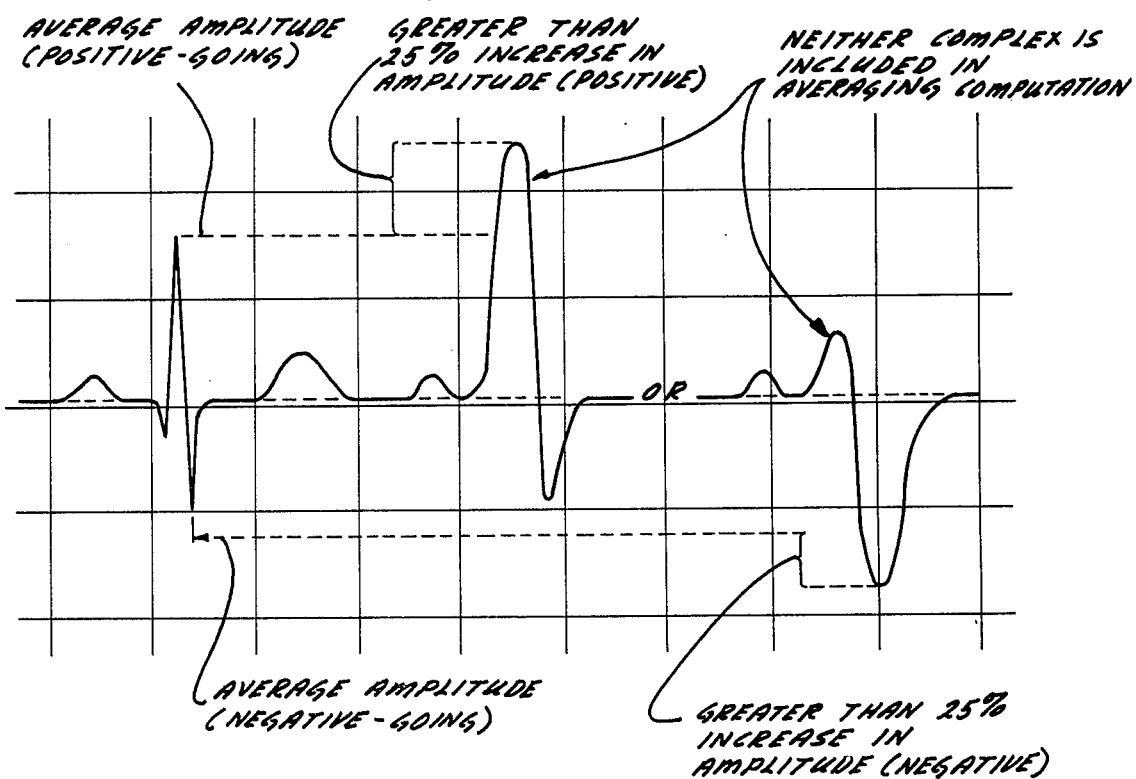
FIG. 20 illustrates a typical ECG complex as compared with ECG complexes having abnormalities in the amplitude of the QRS segment.

In addition to the width criteria, the analyzer of FIG. 18 also provides an amplitude criteria which also must be satisfied if the ECG complex is to be counted as a PVC. Specifically, the amplitude of the QRS segment either positive or negative, must have an increase of more than 25% as compared to the average QRS amplitudes which have preceded the ECG complex being analyzed. The comparator 472 stores the average number of positive and negative amplitudes of the QRS segments of the preceding 10 complexes and compares that with the latest ECG complex to produce an output signal when the ECG complex is ±25% greater than the preceding average. The comparator 472 constantly updates so that each complex is not counted as a PVC, but only when it exceeds by a selected amount, the average of the preceding ten. An amplitude setting 484 is used to control the desired level by which the ECG complex must exceed the previous ten and ±25 is merely representative. Comparator 472 may consist of standard sample and hold circuits which hold the amplitude peak of an R wave in an analog memory circuit such as a capacitor. A value of 25% of this peak is divided down by resistors then supplied to standard comparators which measure any input value to the other input in excess of 25% of the reference input. FIG. 20 illustrates this second criteria and shows an average ECG complex having average positive and negative going QRS portions, which average complex is then followed by two typical complexes which have excessive positive or negative going portions. The comparator 472 also produces an output signal when the ECG complex has a positive going QRS portion.

The third criteria may be at the option of the operator through the use of a switch 486. This switch 486 may be included on the front panel and this criteria is termed as prematurity. Specifically, the comparator 476 provides an output signal representative of prematurity if a normal beat is followed by another beat in a shorter period than normal. Comparator 476 may consist of a standard one-shot that is set for a specific time interval, normally shorter than a normal R to R time period. If an R wave is premature by an amount less than the period of the one-shot, then an output exists using standard AND gates to compare states. All three of these criteria are coupled to an AND gate 488 and all the conditions must be met before the AND gate provides an output. The output from the AND gate is coupled to a register 490 for storing the PVCs and the output of the storage register 490 is provided to the printer and to the PVC display 464. The output from the storage register 490 is controlled by a one hour timing signal from the time clock and with the information coupled to the display and printer controlled by a switch 48. The reset button 468 provides reset to zero at any time. The AND gate 488 also is coupled through an event counter 492 which is controlled by one of a pair of switches 46 to provide an event output when the number of PVCs per minute exceeds a predetermined number.

In order for an ECG complex to be counted as an SVT, four criteria must be met which are established by the comparators 478 and 480 in addition to comparators 472 and 474. As a first criteria, the suspected SVT must occur as a paroxysmal (sudden) tachycardia of a rate more than 140 beats per minute as provided by an output signal from comparator 478. As a second criteria, the average rate of the normal complexes preceding the onset of tachycardia must not exceed 110 beats per minute, or the SVT section of the analyzer will be deactivated until the normal rate returns to a rate lower than 110 beats per minute. This is provided by the comparator 480. It can be seen that the comparator 478 provides an output signal when the rate is greater than 140 beats per minute and the comparator 480 provides an output signal when the preceding normal complexes are less than 110 beats per minute. Comparators 478 and 480 may consist of standard one-shots with a time period equivalent to 110 or 140 beats per minute. If an R wave comes at a rate over 110 or 140 then standard AND gates provide outputs.

As a third criteria, the output from the comparator 472 representing a positive going QRS must be present and as a fourth criteria a width of less than 80 milliseconds for the R wave must be provided by the comparator 474. The outputs from the comparators 472, 474, 478 and 480 are coupled to an AND gate 494, and when all four inputs coincide, the AND gate 494 produces an output signal representative of an SVT.

This SVT output signal is coupled to a storage register 496 to store information in a similar manner to the storage register 490 and with the storage register controlled by either the manual reset 468, or the reset provided by the one hour time signal as controlled by switch 48. The output from the storage register 496 is coupled to the SVT digital display 466 and to the printer for printing on the paper chart the number of such SVTs on an hour-by-hour basis. The output from the AND gate is also coupled to an event counter 498 which provides control of the event marker to indicate when the number of PVCs per minute have exceeded a predetermined amount as selected by switch 46.

The reset switch 48 controls the storage registers 490 and 496 so that with the switch in the one hour position, ectopic beats of either PVC or SVT are displayed as they occur continuously on the PVC and SVT displays 464 and 466. However, at the end of each hour, the presentations are reset to zero. When the switch 48 is placed in the total position, ectopic beats are displayed as they occur, but with the display cumulative and continuously totaled without zeroing at the start of each hour. It is to be appreciated that the storage registers 490 and 496 may actually store the number of ectopic beats continuously even though the registers are zeroed so that by switching from the one hour position to the total position, the displays may provide the cumulative number of beats at any time. The printer 14 which provides the digital printout of the ectopic beats, provides the number of such beats for each hour and may either be controlled to provide such printout on an hour-by-hour basis or a cumulative basis.

As indicated above, the event per minute switches 46 select the maximum rate per minute occurrence of the ectopic beats beyond which the PVC or SVT event markers will mark the chart paper as shown in FIG. 13. For example, if the event per minute switch 46 is set at three, and three or more PVCs occur within a minute, the event marker 402 shown in FIG. 14 will mark the chart, as shown in FIG. 13, to provide a mark of the event.

Figure 21:
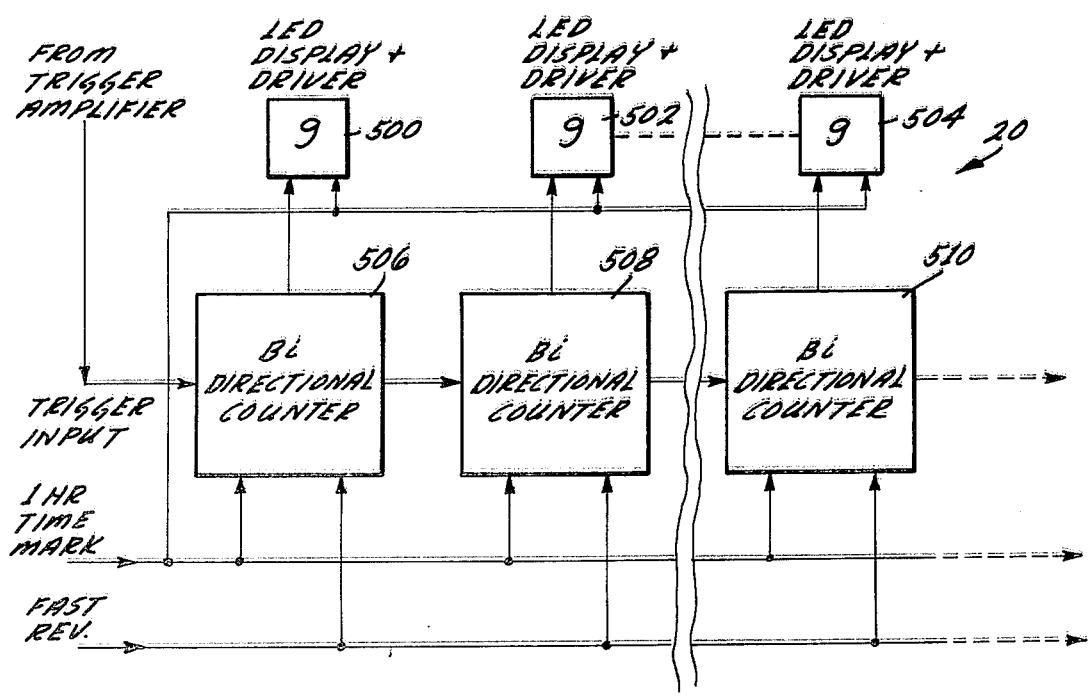
FIG. 21 illustrates a block diagram of a heartbeat totalizer including a heartbeat totalizer display.

The final module shown in the front panel of FIG. 1 is the heartbeat computer 20, and this computer is shown in more detail in FIG. 21. Specifically, the heartbeat computer provides the number of heartbeats recorded on the original recording tape and these heartbeats can be totalized either on an hour-by-hour basis, or on a cumulative basis. This hour-by-hour or cumulative heartbeat data can be displayed using a plurality of display indicators 500, 502, up to any additional number of indicators. The display 504 is shown to be the last display. The heartbeat counter is used to count, in a bidirectional mode, the total number of heartbeats so that an exact ECG complex may be located at any given time. For example, a specific number relating to a particular ECG complex is located by viewing the tape at the slow speed and then observing the heartbeat counter number corresponding to the particular complex. After any further viewing or playing at high speed or even in the fast forward or fast reverse mode, the particular complex can be located by the particular heartbeat counter number.

In FIG. 21, the trigger input from FIG. 8 is applied to the system and since the trigger input corresponds to the R wave in each ECG complex, a single pulse output is provided for each complex. This single pulse for each complex occurs no matter whether the tape transport is moved in any of its speeds, such as X1, X30, X60 or X120, or in the Fast Forward or Fast Reverse modes. The tripper input is coupled to a plurality of bidirectional counters 506, 508 and up to any additional number of counter. The final bidirectional counter is shown as number 510. The counters provide the output signals for the displays 500, 502 and 504. The number of displays correspond in number to the number of counters. Each counter also has an input from the tapedeck when in the fast reverse mode, so that the counter provides for the subtraction of the pulses rather than an addition. A one hour time mark from the clock system is inputted into the counters so as to provide for total heartbeats on an hour-by-hour basis. The one hour time mark has also been shown to be used to provide for controlling information either into a display or into the printer. The displays may be of the type which includes a latch so that the information is maintained until reset or until the next one hour time signal, or the displays can provide a continuous output showing the total number of heartbeats.

The present invention as described above provides for a multispeed ECG scanning device which analyzes ECG complexes to provide outputs of such ECG complexes either in real time, in high speed playback with superimposition of two channels of ECG information, or with high speed playback with trend information of heart rate and ST level. The system is controlled by a digital clock driven by the movement of the tape and provides the number of heartbeats either on an hour-by-hour or a total basis, and provides the number of PVCs and SVTs either on an hour-by-hour or total basis, and provides variable control of speeds and time base of the above factors. In addition, the ECG scanner provides printout of the trend information and printout of particular events such as PVCs and SVTs exceeding a predetermined number of events per minute, and with a digital printout of the time and the actual number of PVCs and SVTs.

Although the invention has been described with reference to a particular embodiment, it is to be appreciated that other variations and adaptations may be made and the invention is only to be limited by the apended claims.

I claim:

1. A dynamic multispeed ECG for reproducing ECG information contained on a recording medium recorded at a particular speed, including
    a plurality of readout positions,
    first means for moving the recording medium past the plurality of readout positions,
    second means coupled to the first means for controlling the first means to move the recording medium at a plurality of speeds including a movement at a particular speed corresponding to the particular speed of recording and including movements of the recording medium at more than one speed greater than the particular speed to provide real time and multispeed high speed playbacks of the recorded information,
    third means located at a first one of the readout positions for reproducing the recorded information when the first means moves the recording medium to provide real time playback,
    fifth means coupled to the third and fourth means and responsive to the control of the playback speed by the second means for compensating the reproduced information for frequency and amplitude variations in accordance with the different speeds, and
    sixth means coupled to the fifth means and responsive to the compensated reproduced information for producing a visual indication of the reproduced information.

2. The ECG computer of claim 1 wherein playback of the different speeds produces timing changes and additionally including seventh means coupled to the third, fourth and sixth means and responsive to the control of the playback speed by the second means for compensating the visual indication produced by the sixth means in accordance with the timing changes produced in accordance with playback at the different speeds.

3. The ECG computer of claim 1 wherein the sixth means includes a scanning display and a sweep speed control responsive to the control of the playback speed by the second means for providing superimposed images of succeeding ECG complexes when the playback of the recorded information is at any one of the high speed playback speeds.

4. The ECG computer of claim 3 wherein the fourth means includes first and second spaced playback means and with the first playback means producing a trigger signal in accordance with the R wave portion of the ECG information and with the second playback means reproducing the ECG information at a point in time after the first playback means produces the trigger signal to provide for triggering the scanning display to provide complete superimposed images of the ECG complexes and additionally including a variable delay means coupled to the first one of the playback means to control the initial display point in the superimposed ECG complex.

5. The ECG computer of claim 3 wherein the first means moves the recording medium for playback past the fourth means and then past the third means to provide a delay in the reproduction of the information by the third means relative to the fourth means and including switching means for switching from the visual indication of the superimposed ECG information reproduced at high playback speed to the visual indication of the ECG information reproduced in real time before the recording medium reaches the third means.

6. The ECG computer of claim 5 wherein the sixth means additionally includes a paper writer for reproducing the ECG complexes reproduced in real time.

7. The ECG computer of claim 5 wherein the first means includes a path for the recording medium having an adjustable length and additionally including a control member for adjustable length of the path to control the amount of delay between the reproduction of the information by the third means relative to the fourth means.

8. The ECG computer of claim 1 wherein the recording medium contains two tracks of ECG information representing the same heart muscle activity viewed from two different positions and wherein the sixth means includes plural inputs for producing a visual indication of both tracks of ECG information.

9. The ECG computer of claim 8 wherein the third means includes at least a two-track playback head having separate U-shaped pole members for reproducing information from each track and with each U-shaped pole member including a coil and with the coils surrounding opposite legs of the pole members and including a Z shaped shield member positioned between the U-shaped pole members including the coils.

10. The ECG computer of claim 8 wherein the sixth means includes a scanning display, a sweep speed control responsive to its control of the playback speed by the second means and a means for laterally displaying images on the scanning display for providing superimposed images of succeeding ECG complexes of both tracks of ECG information and with the superimposed images laterally displaced one above the other when the playback of the recorded information is at any one of the high speed playback speeds.

11. The ECG computer of claim 10 wherein the sixth means additionally includes means for producing superimposition of the superimposed images for direct comparison of the superimposed ECG complexes.

12. The ECG computer of claim 10 additionally including a seventh means coupled to the fourth means and responsive to successive ECG complexes each including an R wave which complexes are reproduced during high speed playback for producing an output signal representative of the R wave to R' wave interval between successive ECG complexes and with the sixth means responsive to such output signal for producing an arrhythmia bar graph laterally displaced from the superimposed ECG images.

13. The ECG computer of claim 1 wherein the first means includes a pair of motors to control the supply and take-up of the recording medium during reproduction of the ECG information and with one of the motors providing a force to take-up the recording medium and the other of the motors providing a force for braking in the take-up of the recording medium in accordance with the direction of movement of the recording medium and additionally including seventh means responsive to the control of the speed of the recording medium by the second means for varying the forces for take-up and braking provided by the motors in accordance with the speed of the recording medium.

14. The ECG computer of claim 13 additionally including eighth means responsive to the movement of the recording medium at the different speeds for producing a clock pulse related to the speed of recording each time the recording medium is moved a predetermined distance irregardless of the speed or direction of movement, and additionally including ninth means responsive to the clock pulses for producing an output indication of time as related to the recording time of the recording medium.

15. The ECG computer of claim 14 wherein the ninth means additionally includes means for presetting the output indication of time to the initial time of the start of the recording of the recording medium.

16. The ECG computer of claim 15 wherein the sixth means includes a paper writer having a digital printout for printing out on a periodic basis the time of recording.

17. The ECG computer of claim 1 additionally including seventh means coupled to the fourth and sixth means and responsive to particular characteristics of the ECG information reproduced at high speed playback for producing output signals in accordance with the trend of the particular characteristics of the ECG complexes at high speed playback and with the sixth means producing a visual indication of such output signals.

18. The ECG computer of claim 17 wherein the sixth means includes a paper writer for reproducing the trend output signals to form a trend chart and with the speed of operation of the paper writer equal to a small fraction of the speed of playback of the recording medium.

19. The ECG computer of claim 18 wherein the seventh means is responsive to heart beat rate and ST level for producing trend output signals representing heart beat rate and ST level and wherein the paper writer provides a two channel writeout of the trend information on the trend chart.

20. The ECG computer of claim 18 additionally including eighth means for producing a digital printout of time related to the time of recording on a periodic basis on the trend chart.

21. The ECG computer of claim 18 additionally including eighth means coupled to the fourth means for sensing ectopic beats in the ECG information reproduced at high speed playback and additionally including ninth means responsive to the sensed ectopic beats for producing a digital printout of the number of such ectopic beats in at predetermined periods of time on a periodic basis on the trend chart.

22. The ECG computer of claim 21 wherein the eighth means sense PVC and SVT ectopic beats and wherein the ninth means produces separate printout of the individual totals of PVC and SVT ectopic beats.

23. The ECG computer of claim 21 wherein the eighth means additionally includes means for producing an output signal in accordance with the number of ectopic beats exceeding a predetermined number in a predetermined unit time and with the paper writer including additional marking means responsive to such output signal for marking the trend chart in accordance with the output signal.

24. The ECG computer of claim 18 additionally including means for operating the paper writer at different speeds in accordance with the speed of playback for producing a constant length for the trend chart for a given length of recording medium irregardless of the speed of playback.

25. The ECG computer of claim 1 additionally including seventh means coupled to the fourth means for sensing ectopic beats in the ECG information reproduced at high speed playback and additionally including eighth means responsive to the sensed ectopic beats for producing a digital display of the number of such ectopic beats in a predetermined period of time.

26. The ECG computer of claim 25 wherein the eighth means includes means for switching the display between an hour-by-hour and a cumulative basis.

27. The ECG computer of claim 25 wherein the seventh means senses PVC and SVT ectopic beats and wherein the eighth means produces separate display of the individual totals of PVC and SVT ectopic beats.

28. The ECG computer of claim 1 additionally including seventh means responsive to the third and fourth means for producing an output pulse for each reproduced ECG complex and additionally including eighth means for counting the heart beats by producing a digital display of the number of reproduced heart beats.

29. The ECG computer of claim 28 wherein the first means includes means for moving the recording medium in forward and reverse directions and additionally including means for controlling the digital display between an additive and a subtractive state in accordance with the direction of movement of the recording medium.

30. The ECG computer of claim 28 wherein the eighth means includes means for switching the display between an hour-by-hour and a cumulative basis.

31. A dynamic multispeed ECG computer for reproducing ECG information contained on a recording medium recorded at a particular speed, including
a readout position,
first means for moving the recording medium past the readout position,
second means coupled to the first means for controlling the first means to move the recording medium at a plurality of speeds and at least speeds greater than the particular speed to provide multispeed high speed playbacks of the recorded information,
third means located at the readout position for reproducing the recorded information when the first means moves the recording medium to provide the plurality of high speed playbacks.
fourth means coupled to the third means and responsive to the control of the playback speed by the second means for compensating the reproduced information for frequency and amplitude variations in accordance with the different speeds, and
fifth means including a sweep speed control responsive to the control of the playback speed by the second means and a scanning display coupled to the fourth means and responsive to the compensated reproduced information for producing superimposed images of succeeding ECG complexes when the playback of the recorded information is at any one of the high speed playback speeds.

32. The ECG computer of claim 31 wherein the third means includes first and second spaced playback means and with the first playback means producing a trigger signal in accordance with the R wave portion of the ECG information and with the playback means reproducing the ECG information at a point in time after the first playback means produces the trigger signal to provide for triggering the scanning display to provide complete superimposed images of the ECG complexes and additionally including a variable delay means coupled to the first one of the playback means to control the initial display point in the superimposed ECG complex.

33. The ECG computer of claim 31 additionally including sixth means coupled to the third and fifth means and responsive to the control of the playback speed by the second means for compensating the superimposition of the ECG complexes produced by the fifth means in accordance with playback at the different speeds.

34. The ECG computer of claim 31 wherein the recording medium contains two tracks of ECG information representing the same heart muscle activity viewed from two different positions and wherein the fifth means includes plural inputs for producing a superimposition of the ECG complexes of both tracks of ECG information, and with the superimposed images laterally displaced one above the other when the playback of the recorded information is at any one of the high speed playback speeds.

35. The ECG computer of claim 34 wherein the fifth means additionally includes means for producing superimposition of the superimposed images for direct comparison of the superimposed ECG complexes.

36. The ECG computer of claim 34 additionally including a sixth means coupled to the third means and responsive to successive ECG complexes each including an R wave which complexes are reproduced during the plurality of high speed playbacks for producing an output signal representative of the R wave to R'wave interval between successive ECG complexes and with the fifth means responsive to such output signal for producing an arrhythmia bar graph laterally displaced from the superimposed ECG images.

37. The ECG computer of claim 31 additionally including a second readout position for producing readout at real time and wherein the first means moves the recording medium for playback past the third means and then past the second readout position to provide a delay in the reproduction of the information at the second readout position relative to the reproduction by the third means and including switching means for switching from a visual indication of the superimposed ECG information reproduced at high playback speed to a visual indication of the ECG information reproduced in real time before the recording medium reaches the second readout position.

38. The ECG computer of claim 37 wherein the second readout position includes at least a two-track playback head having separate U-shaped pole members for reproducing information from each track and with each U-shaped pole member including a coil and with the coils surrounding opposite less of the pole members and including a Z shaped shield member positioned between the U-shaped pole members including the coils.

39. The ECG computer of claim 37 additionally including a paper writer for reproducing the ECG complexes reproduced in real time.

40. The ECG computer of claim 37 wherein the first means includes a path for the recording medium having an adjustable length and additionally including a control member for adjusting the length of the path to control the amount of delay between the reproduction of the information at the second readout position relative to the readout by the third means.

41. A dynamic multispeed computer for reproducing ECG information contained on a recording medium recorded at a particular speed, including
at least one readout position,
first means for moving the recording medium past the one readout position in a playback direction and in a reverse direction,
second means coupled to the first means for controlling the first means to move the recording medium at a plurality of speeds including a movement at a particular speed in playback direction corresponding to the particular speed of recording and including movements of the recording medium at more than one speed in the playback direction greater than the particular speed to provide real time and multispeed high speed playbacks of the recorded information and at a speed in the reverse direction,
third means location at the readout position for reproducing the recorded information when the first means moves the recording medium at the plurality of speeds,
fourth means coupled to the third means and responsive to the control of the playback speed by the second means for compensating the reproduced information for frequency and amplitude variations in accordance with the different speeds,
fifth means coupled to the fourth means and responsive to the compensated reproduced information for producing a display of the reproduced information, sixth means responsive to the movement of the recording medium for producing a clock pulse related to the speed of recording each time the recording medium is moved a predetermined distance irregardless of the speed or direction of movement, and additionally including seventh means responsive to the clock pulses for producing an output indication of time as related to the recording time of the recording medium.

42. The ECG computer of claim 41 wherein the first means includes a pair of motors to control the supply and take-up of the recording medium during reproduction of the ECG information and with one of the motors providing a force to take-up the recording medium and the other of the motors providing a force for braking in the take-up of the recording medium in accordance with the direction of movement of the recording medium and additionally including seventh means responsive to the control of the speed of the recording medium by the second means for varying the take-up and braking provided by the motors in accordance with the speed of the recording medium.

43. The ECG computer of claim 41 wherein the seventh means additionally includes means for presetting the output indication of time to the initial time of the start of the recording of the recording medium.

44. The ECG computer of claim 43 wherein the fifth means includes a paper writer having a digital printout for printing out on a periodic basis the time of recording.

45. A dynamic multispeed ECG computer for reproducing ECG information contained on a recording medium recorded at a particular speed, including at least one readout position first means for moving the recording medium past the one readout position, second means coupled to the first means for controlling the first means to move the recording medium at a plurality of speeds including a movement of the recording medium at a plurality of playback speeds greater than the particular speed to provide multispeed high speed playbacks of the recorded information, third means located at the readout positions for reproducing the recorded information when the first means moves the recording medium to provide high speed playback at the plurality of playback speeds, fourth means coupled to the third means for sensing PVC and SVT ectopic beats in the ECG information produced at high speed playback for producing output signals in accordance with the PVC and SVT ectopic beats, and fifth means coupled to the fourth means and responsive to the output signals for producing a separate visual indication of the PVC and SVT ectopic beats.

46. The ECG computer of claim 45 additionally including sixth means for producing a digital display of the number of the PVC and SVT ectopic beats in a predetermined period of time.

47. The ECG computer of claim 46 wherein the sixth means includes means for switching the digital display between an hour-by-hour and a cumulative basis.

48. A dynamic multispeed ECG computer for reproducing ECG information contained on a recording medium at a particular speed, including a plurality of readout positions, first means for moving the recording medium past the plurality of readout positions and with the first means including means for moving the recording medium in forward and reverse directions, second means coupled to the first means for controlling the first means to move the recording medium at a plurality of speeds including a forward movement at a particular speed corresponding to the particular speed of recording and including forward movements of the recording medium at more than one speed greater than the particular speed to provide real time and multispeed high speed playbacks of the recorded information, and including a reverse movement of at least one speed greater than the particular speed, third means located at a first one of the readout positions for reproducing the recorded information when the first means moves the recording medium to provide real time playback, fourth means located at a second one of the readout positions for reproducing the recorded information when the first means moves the recording medium to provide high speed movement in either the forward or reverse directions, fifth means coupled to the third and fourth means and responsive to the control of the playback speed by the second means for producing an output pulse for each reproduced ECG complex, and sixth means coupled to the fifth means and responsive to the output pulses for counting the output pulses by producing a digital display of the number of reproduced heart beats.

49. The ECG computer of claim 48 additionally including means for controlling the digital display between an additive and a subtractive state in accordance with the direction of movement of the recording medium provided by the first means.

50. The ECG computer of claim 48 wherein the sixth means includes means for switching the display between an hour-by-hour and a cumulative basis.

51. A dynamic multispeed ECG computer for reproducing ECG information contained on a recording medium recorded at a particular speed, including a plurality of readout positions, first means for moving the recording medium past the plurality of readout positions, second means coupled to the first means for controlling the first means to move the recording medium at a plurality of speeds including a movement at a particular speed corresponding to the particular speed of recording and including movements of the recording medium at more than one speed greater than the particular speed to provide real time and multispeed high speed playbacks of the recorded information, third means located at a first one of the readout positions for reproducing the recorded information when the first means moves the recording medium to provide high speed playback, fourth means located at a second one of the readout positions for reproducing the recorded information when the first means moves the recording medium to provide high speed playback, fifth means coupled to the third and fourth means and responsive to the control of the playback speed by the second means for producing different timing signals in accordance with the different speeds, and sixth means coupled to the third, fourth and fifth means and responsive to the reproduced information for producing a visual indication of the reproduced information and responsive to the different timing signals for compensating the visual indication for the different timing signals produced in accordance with the playback at the different speeds.

52. The ECG computer of claim 51 wherein the sixth means includes a scanning display and a sweep speed control responsive to the control of the playback speed by the second means for providing superimposed images of succeeding ECG complexes when the playback of the recorded information is at any one of the high speed playback speeds and additionally including means for compensating the scanning rate in accordance with the different timing signals to provide the same superimposed image at different speeds.

53. The ECG computer of claim 51 wherein the fourth means includes first and second spaced playback means and with the first playback means producing a trigger signal in accordance with the R wave portion of the ECG information and with the second playback means reproducing the ECG information at a point in time after the first playback means produces the trigger signal to provide for triggering the scanning display to provide complete superimposed images of the ECG complexes and additionally including a variable delay means coupled to the first one of the playback means to control the initial display point in the superimposed ECG complex.

54. The ECG computer of claim 51 wherein the recording medium includes two tracks of ECG information and wherein the sixth means includes a scanning display and a sweep speed control responsive to the control of the playback speed by the second means for providing superimposed images of succeeding ECG complexes of the two tracks of ECG information recorded on the recording medium and with the superimposed images laterally displaced one above the other when the playback of the recorded information is at any one of the high speed playback speeds and additionally including means for compensating the scanning rate in accordance with the different timing signals to provide the same superimposed image at different speeds.

55. The ECG computer of claim 54 wherein the sixth means additionally includes means for producing superimposition of the superimposed images for direct comparison of the superimposed ECG complexes.

56. The ECG computer of claim 54 additionally including a seventh means coupled to the fourth means and responsive to successive ECG complexes each including an R wave which complexes are reproduced during high speed playback for producing an output signal representative of the R wave to R' wave interval between successive ECG complexes and with the sixth means responsive to such output signal for producing an arrhythmia bar graph laterally displaced from the superimposed ECG images and with the different timing signals providing for the same arrhythmia bar graph at different speeds.

57. The ECG computer of claim 51 additionally including seventh means coupled to the fourth, fifth and sixth means and responsive to particular characteristics of the ECG information reproduced at high speed playback for producing output signals in accordance with the trend of the particular characteristics of the ECG complexes at high speed playback and with the sixth means producing a visual indication of such output signal and responsive to the different timing signals to compensate for different playback speeds.

58. The ECG computer of claim 57 wherein the sixth means includes a paper writer for reproducing the trend output signals to form a trend chart and with the speed of operation of the paper writer equal to a small fraction of the speed of playback of the recording medium.

59. The ECG computer of claim 58 wherein the seventh means includes means responsive to heart beat rate and ST level for producing trend output signals representing heart beat rate and ST level and wherein the paper writer includes a two channel writeout for providing a separate channel on the trend chart for the heart beat rate and ST level.

60. The ECG computer of claim 58 additionally including eighth means for producing a digital printout of time related to the time of recording on a periodic basis on the trend chart and additionally including means for controlling the timing of the digital printout in accordance with the different timing signals.

61. The ECG computer of claim 58 additionally including eighth means coupled to the fourth means for sensing ectopic beats in the ECG information reproduced at high speed playback and additionally including ninth means responsive to the sensed ectopic beats for producing a digital printout of the number of such ectopic beats in a predetermined period of time on a periodic basis on the trend chart and with the different timing signals controlling the timing of the digital printout.

62. The ECG computer of claim 58 additionally including means for operating the paper writer at different speeds in accordance with the different timing signals to produce a constant length for the trend chart for a given length of recording medium irregardless of the speed of playback.

63. A dynamic multispeed ECG computer for reproducing ECG information contained on a recording medium recorded at a particular speed, including
   at least one readout position,
   first means for moving the recording medium past the one readout position,
   second means coupled to the first means for controlling the first means to move the recording medium at a plurality of speeds including at least a movement of the recording medium at more than one speed greater than the particular speed to provide multispeed high speed playbacks of the recorded information,
   third means located at the one readout position for reproducing the recorded information when the first means moves the recording medium to provide high speed playback at the plurality of speeds,
   fourth means coupled to the third means and responsive to particular characteristics of the ECG information reproduced at high speed playback for producing output signals in accordance with the trend of the particular characteristics of the ECG complexes at high speed playback,
   fifth means coupled to the fourth means and responsive to the output signals for producing a visual indication of the trend information at the different playback speeds, said fifth means including a paper writer for reproducing the trend output signals to form a trend chart and with the speed of operation of the paper writer equal to a small fraction of the speed of the playback of the recording medium, sixth means coupled to the third means for sensing ectopic beats in the ECG information reproduced at high speed playback and additionally including seventh means responsive to the sensed ectopic beats for producing a digital printout of the number of such ectopic beats in at predetermined periods of time on a periodic basis on the trend chart, the said sixth means sensing PVC and SVT ectopic beats, and said seventh means producing separate printout of the individual totals of the PVC and SVT ectopic beats.

64. A dynamic multispeed ECG computer for reproducing ECG information contained on a recording medium recorded at a particular speed, including at least one readout position, first means for moving the recording medium past the one readout position, second means coupled to the first means for controlling the first means to move the recording medium at a plurality of speeds including at least a movement of the recording medium at more than one speed greater than the particular speed to provide multispeed high speed playbacks of the recorded information, third means located at the one readout position for reproducing the recorded information when the first means moves the recording medium to provide high speed playback at the plurality of speeds, fourth means coupled to the third means and responsive to particular characteristics of the ECG information reproduced at high speed playback for producing output signals in accordance with the trend of the particular characteristics of the ECG complexes at high speed playback, fifth means coupled to the fourth means and responsive to the output signals for producing a visual indication of the trend information at the different playback speeds, said fifth means including a paper writer for reproducing the trend output signals to form a trend chart and with the speed of operation of the paper writer equal to a small fraction of the speed of the playback of the recording medium, and means for operating the paper writer at different speeds in accordance with the speed of the playback for reproducing a constant length for the trend chart for a given length of recording medium regardless of the speed of playback.

* * * * *

UNITED STATES PATENT AND TRADEMARK OFFICE
CERTIFICATE OF CORRECTION

PATENT NO. : 4,006,737
DATED : February 8, 1977
INVENTOR(S) : Isaac Raymond Cherry It is certified that error appears in the above-identified patent and that said Letters Patent are hereby corrected as shown below:

In Column 33, after line 65 insert:

--fourth means located at a second one of the readout positions for reproducing the recorded information when the first means moves the recording medium to provide high speed playback,--

Signed and Sealed this second Day of August 1977

[SEAL]

Attest:

RUTH C. MASON
*Attesting Officer*

C. MARSHALL DANN
*Commissioner of Patents and Trademarks*